(12) United States Patent
Chang

(10) Patent No.: US 9,127,066 B2
(45) Date of Patent: *Sep. 8, 2015

(54) METHODS FOR TREATING OSTEOPOROSIS WITH ANTI-IL-20 RECEPTOR ANTIBODIES

(75) Inventor: Ming-Shi Chang, Tainan (TW)

(73) Assignee: National Cheng Kung University, Tainan (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/087,502

(22) Filed: Apr. 15, 2011

(65) Prior Publication Data

US 2011/0256093 A1 Oct. 20, 2011

Related U.S. Application Data

(60) Provisional application No. 61/324,820, filed on Apr. 16, 2010.

(51) Int. Cl.
| | |
|---|---|
| A61K 39/395 | (2006.01) |
| C07K 16/28 | (2006.01) |
| A61K 31/7088 | (2006.01) |
| A01K 67/027 | (2006.01) |
| C07K 14/715 | (2006.01) |

(52) U.S. Cl.
CPC ......... *C07K 16/2866* (2013.01); *A01K 67/0276* (2013.01); *A61K 31/7088* (2013.01); *C07K 14/7155* (2013.01); *A01K 2217/075* (2013.01); *A01K 2227/105* (2013.01); *A01K 2267/035* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,585,089 | A | 12/1996 | Queen et al. |
| 5,888,510 | A | 3/1999 | Kishimoto et al. |
| 7,189,394 | B2 * | 3/2007 | Thompson et al. ........ 424/130.1 |
| 7,435,800 | B2 | 10/2008 | Chang |
| 7,611,705 | B2 * | 11/2009 | Chang ........................ 424/141.1 |
| 7,837,994 | B2 * | 11/2010 | Chang ........................ 424/133.1 |
| 8,012,478 | B2 * | 9/2011 | Chang ........................ 424/133.1 |
| 8,377,441 | B2 | 2/2013 | Chang |
| 8,454,956 | B2 * | 6/2013 | Chang ........................ 424/130.1 |
| 8,535,674 | B2 | 9/2013 | Chang |
| 2002/0151532 | A1 | 10/2002 | Kagan et al. |
| 2003/0148955 | A1 | 8/2003 | Pluenneke |
| 2004/0235728 | A1 | 11/2004 | Stoch et al. |
| 2004/0235808 | A1 | 11/2004 | Wang |
| 2005/0143333 | A1 | 6/2005 | Richards et al. |
| 2005/0170468 | A1 | 8/2005 | Xu et al. |
| 2006/0142550 | A1 | 6/2006 | Chang |
| 2006/0269551 | A1 | 11/2006 | Thompson et al. |
| 2008/0311115 | A1 | 12/2008 | Chang |
| 2009/0048432 | A1 | 2/2009 | Chang |
| 2011/0064731 | A1 * | 3/2011 | Chang ........................ 424/133.1 |
| 2011/0305698 | A1 | 12/2011 | Chang |
| 2011/0305699 | A1 | 12/2011 | Chang |

FOREIGN PATENT DOCUMENTS

| | | |
|---|---|---|
| EP | 2050458 A1 | 4/2009 |
| WO | WO 2010/042634 A1 | 4/2010 |

OTHER PUBLICATIONS

Holliger et al. "Diabodies": Small bivalent and bispecific antibody fragments. Proc. Natl. Acad. Sci. U.S.A., 1993, 90(14): 6444-6448.*
Chen et al. IL-20 is regulated by hypoxia-inducible factor and up-regulated after experimental ischemic stroke. J Immunol. Apr. 15, 2009; 182(8):5003-12.*
Fisher, P. Is mda-7/IL-24 a "Magic Bullet" for Cancer? Cancer Res. 2005;65:10128-10138.*
Li et al. Interleukin-20 induced cell death in renal epithelial cells and was associated with acute renal failure. Genes and Immunity (2008) 9, 395-404.*
Alanara et al., Expression of IL-10 family cytokines in rheumatoid arthritis: elevated levels of IL-19 in the joints. Scand J Rheumatol. Mar. 2010;39(2):118-26.
Chuntharapai et al., Generation of monoclonal antibodies to chemokine receptors. Methods Enzymol. 1997;288:15-27.
Hsing et al., The distribution of interleukin-19 in healthy and neoplastic tissue. Cytokine. Nov. 2008;44(2):221-8. Epub Sep. 21, 2008.
Jung et al., Analysis of the expression profiles of cytokines and cytokine-related genes during the progression of breast cancer growth in mice. Oncol Rep. Nov. 2009;22(5):1141-7.
Genbank Submission, Accession No. AAK84423; Rieder et al.; Aug. 9, 2001. Last accessed on Jul. 18, 2012 at http://www.ncbi.nlm.nih.gov/protein/15128211. 1 page.
Sakurai et al., Expression of IL-19 and its receptors in RA: potential role for synovial hyperplasia formation. Rheumatology (Oxford). Jun. 2008;47(6):815-20. Epub Apr. 8, 2008.
Hör et al., "The T-cell Lymphokine Interleukin-26 Targets Epithelial Cells through the Interleukin-20 Receptor 1 and Interleukin-10 Receptor 2 Chains," J Biol Chem., Aug. 6, 2004, vol. 279, No. 32, pp. 33343-33351.
International Search Report and Written Opinion for PCT/US2011/032657 mailed Dec. 26, 2011.
Zheng et al., " Human interleukin 24 (MDA-7/IL-24) protein kills breast cancer cells via the IL-20 receptor and is antagonized by IL-10," Cancer Immunol Immunother, 2007 (month unknown), vol. 56, pp. 205-215.

(Continued)

*Primary Examiner* — Dong Jiang

(74) *Attorney, Agent, or Firm* — Wolf, Greenfield & Sacks, P.C.

(57) ABSTRACT

Treating a disorder (e.g., osteoporosis, renal failure, or diabetic nephropathy) associated with a signaling pathway mediated by IL-20 receptor with an agent that suppresses IL-20 receptor activity, e.g., an antibody that neutralizes IL-20 receptor via binding to IL-20R1, an antisense nucleic acid that suppresses expression of IL-20R1, a small molecule that inhibits IL-20 receptor activity, or a dominant negative mutant of IL-19, IL-20, or IL-24.

7 Claims, 7 Drawing Sheets

(56) References Cited

OTHER PUBLICATIONS

Williams et al., Tumor angiogenesis as a prognostic factor in oral cavity tumors, 1994, American Journal of Surgery, vol. 168, p. 373-380.

Baselga, The EGFR is a target for anticancer therapy—focus on cetuximab, 2001, European Journal of Cancer, vol. 37, S16-S22.

Baird et al., IL-20 is epigenetically regulated in NSCLC and down regulates the expression of VEGF. Eur J Cancer. Aug. 2011;47(12):1908-18. doi: 10.1016/j.ejca.2011.04.012. Epub May 10, 2011.

Banerjee et al., Deregulated cyclooxygenase-2 expression in oral premalignant tissues. Mol Cancer Ther. Dec. 2002;1(14):1265-71.

Heuzé-Vourc'h et al., IL-20, an anti-angiogenic cytokine that inhibits COX-2 expression. Biochem Biophys Res Commun Jul. 29, 2005;333(2):470-5.

Howe et al., Cyclooxygenase-2: a target for the prevention and treatment of breast cancer. Endocr Relat Cancer. Jun. 2001;8(2):97-114.

Hsieh et al., Interleukin-20 promotes angiogenesis in a direct and indirect manner. Genes Immun. Apr. 2006;7(3):234-42.

Hsing et al., Tissue microarray analysis of interleukin-20 expression. Cytokine. Jul. 2006;35(1-2):44-52. Epub Sep. 5, 2006.

Balmaña et al., ESMO Guidelines Working Group. BRCA in breast cancer: ESMO clinical recommendations. Ann Oncol. May 2009;20 Suppl. 4: 19-20.

Body et al., A study of the biological receptor activator of nuclear factor-kappaB ligand inhibitor, denosumab, in patients with multiple myeloma or bone metastases from breast cancer. Clin Cancer Res. Feb. 15, 2006;12(4):1221-8.

Fox et al., Breast cancer angiogenesis. Breast Cancer Resear. 2007;9(216):1-11.

Kataja et al., ESMO Guidelines Working Group. Primary breast cancer: ESMO clinical recommendations for diagnosis, treatment and follow-up. Ann Oncol. May 2009;20 Suppl 4:10-4.

Nelson et al., U.S. Preventive Services Task Force. Screening for breast cancer: an update for the U.S. Preventive Services Task Force. Ann Intern Med. Nov. 17, 2009;151(10):727-37, W237-42.

Sugerman et al., Current concepts in oral cancer. Aust Dent J. 1999;44(3):147-56.

\* cited by examiner

A.

B.

METHODS FOR TREATING OSTEOPOROSIS WITH ANTI-IL-20 RECEPTOR ANTIBODIES

RELATED APPLICATION

This application claims the benefit of U.S. provisional application No. 61/324,820, filed Apr. 16, 2010 under 35 U.S.C. §119, the entire content of which is incorporated herein by reference.

BACKGROUND OF THE INVENTION

Inflammation is a set of localized nonspecific immune responses elicited by tissue injury. On the one hand, inflammatory responses are protective, as they serve to destroy, dilute, or sequester both the injurious agent and the injured tissue. On the other hand, they have been observed in almost all disease/disorders, either as a contributing factor or as a disease syndrome.

Osteoporosis is a disease characterized by low bone mass and loss of bone tissue, resulting in weak and fragile bones. Renal failure is a disorder in which the kidneys do not function properly. Diabetic nephropathy is a progressive kidney disease associated with longstanding diabetes mellitus. Inflammatory responses have been observed in all of these three diseases.

The IL-20 receptor, a dimeric complex, contains subunits R1 and R2 (also known as RA and RB). It is a common receptor for three functionally different cytokines, i.e., IL-19, IL-20, and IL-24. This suggests that IL-20 receptor can trigger different signaling pathways when activated by different cytokines.

SUMMARY OF THE INVENTION

The present disclosure is based on unexpected discoveries that IL-20R1 knock-out mice (i.e., IL-20 receptor-null mice) developed much less severe osteoporosis, renal failure, and diabetic nephropathy, as compared to their wild-type counterparts and that two monoclonal anti-IL-20R1 antibodies successfully inhibited differentiation of osteoclast cells and IL-19-induced proliferation of CE81T cells.

Accordingly, this disclosure provides a method for treating a disorder associated with a signaling pathway mediated by IL-20 receptor (e.g., osteoporosis, renal failure, diabetic nephropathy, rheumatoid arthritis, cancer such as oral cancer, breast cancer, and esophagus cancer, cancer-induced osteolysis, and ischemic reperfusion or stroke) by administering to a subject in need thereof an effective amount of an agent that suppresses IL-20 receptor activity. The agent can be an antibody that binds to and neutralizes an IL-20 receptor, an antisense nucleic acid of the IL-20 receptor, a dominant negative mutant of IL-19, IL-20, or IL-24, or a small molecule that inhibits the activity of the IL-20 receptor. An antibody capable of neutralizing an IL-20 receptor (i.e., binding to the IL-20 receptor and blocking the signal transduction mediated by the receptor) can be an anti-IL-20R1 antibody. It can be a whole immunoglobulin, an antigen binding fragment thereof, or a genetically engineered antibody (e.g., a humanized antibody, a chimeric antibody, or a single-chain antibody).

In some embodiments, the anti-IL-20R1 antibody used in the treatments disclosed herein is monoclonal antibody mAb7GW, monoclonal antibody mAb51D, an antigen-binding fragment thereof, or a functional equivalent thereof. The anti-IL-20R1 antibody can have (a) a heavy chain variable region containing the same complementarity determining regions (CDRs) as those in the heavy chain variable region of monoclonal antibody mAb7GW or mAb51D, and (b) a light chain variable region containing the same CDRs as those in the light chain variable region of mAb7GW or mAb51D. In one example, it comprises the same heavy chain variable region and the same light chain variable region as mAb7GW or mAb51D.

The mAb7GW and mAb51D antibodies, their antigen-binding fragments and functional equivalents are also within the scope of this disclosure. Functional equivalents of mAb7GW and mAb51D include antibodies having the same heavy chain and light chain CDRs as mAb7GW or mAb51D. In some embodiments, these functional equivalents are genetically engineered antibodies derived from mAb7GW or mAb51D, e.g., chimeric antibodies, single-chain antibodies, or humanized antibodies.

The antisense nucleic acid can be an antisense RNA targeting IL-20R1, e.g., an siRNA or a microRNA that suppresses expression of IL-20R1 via RNA interference.

As used herein, the term "treating" refers to the application or administration of a composition including one or more active agents to a subject, who has a disorder/disease associated with the signaling pathway mediated by IL-20 receptor, a symptom of the disease/disorder, or a predisposition toward the disease/disorder, with the purpose to cure, heal, alleviate, relieve, alter, remedy, ameliorate, improve, or affect the disease/disorder, the symptom of the disease/disorder, or the predisposition toward the disease/disorder.

Also within the scope of this disclosure are (a) a pharmaceutical composition containing one or more agent that suppresses IL-20 receptor activity for use in treating an IL-20 receptor-mediated disorder (e.g., osteoporosis, renal failure, diabetic nephropathy, cancer such as oral cancer and breast cancer, rheumatoid arthritis, and cancer-induced osteolysis), and (b) uses thereof in manufacturing a medicament for the above-listed treatments.

The details of one or more embodiments of the disclosure are set forth in the description below. Other features or advantages of the present disclosure will be apparent from the following drawings and detailed description of several examples, and also from the appended claims.

BRIEF DESCRIPTION OF THE DRAWINGS

The drawings are first described.

Survival rates. Panel C: Serum BUN levels at day 49 post STZ-treatment. Panel D: Glomerular areas determined at day 6 and day 49 post STZ-treatment in IL-20R1$^{+/+}$ mice (n=7), IL-20R1$^{+/-}$ mice (n=7), and IL-20R1$^{-/-}$ (n=5) mice. Values are means±standard error mean. *P<0.05 as compared to IL-20R1$^{+/+}$ mice. Mice treated with saline buffer were used as controls.

Figure 5:
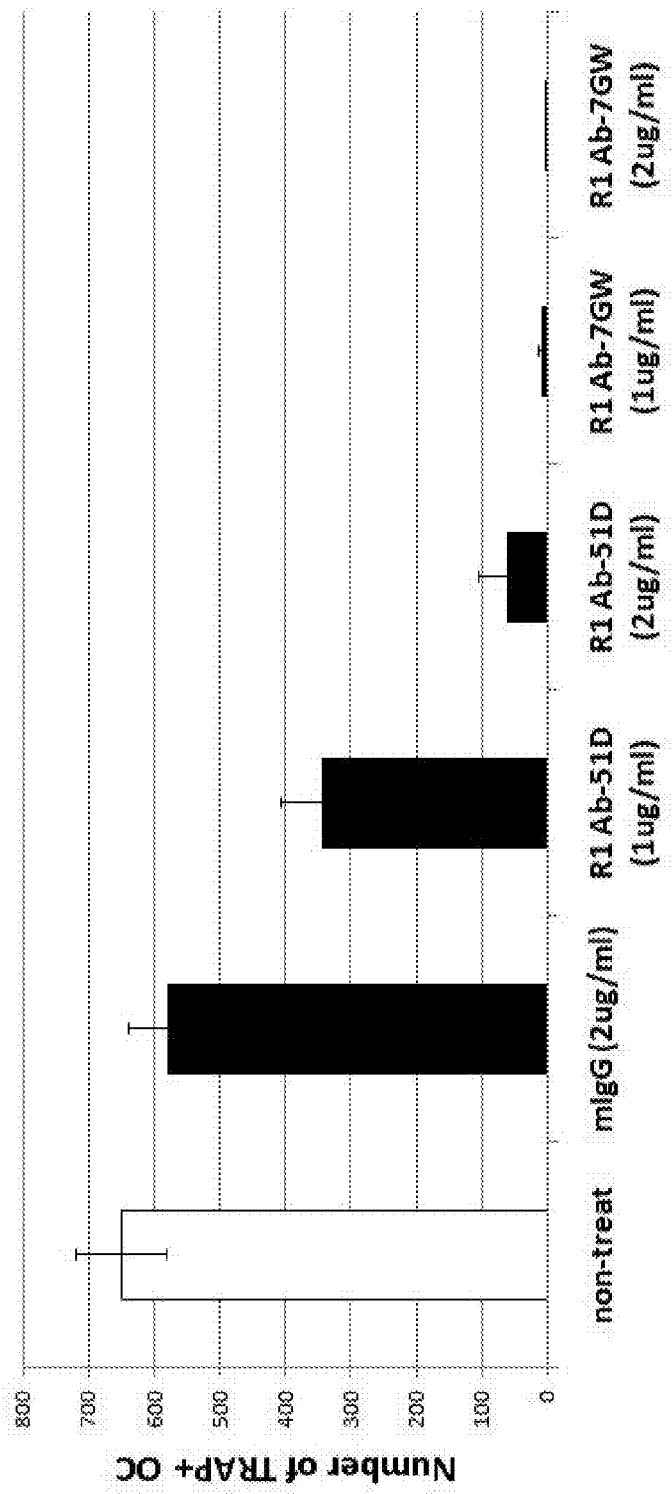

FIG. 5 is a chart showing inhibition of osteoclast differentiation by monoclonal antibodies mAb7GW and mAb51D.

Figure 6:
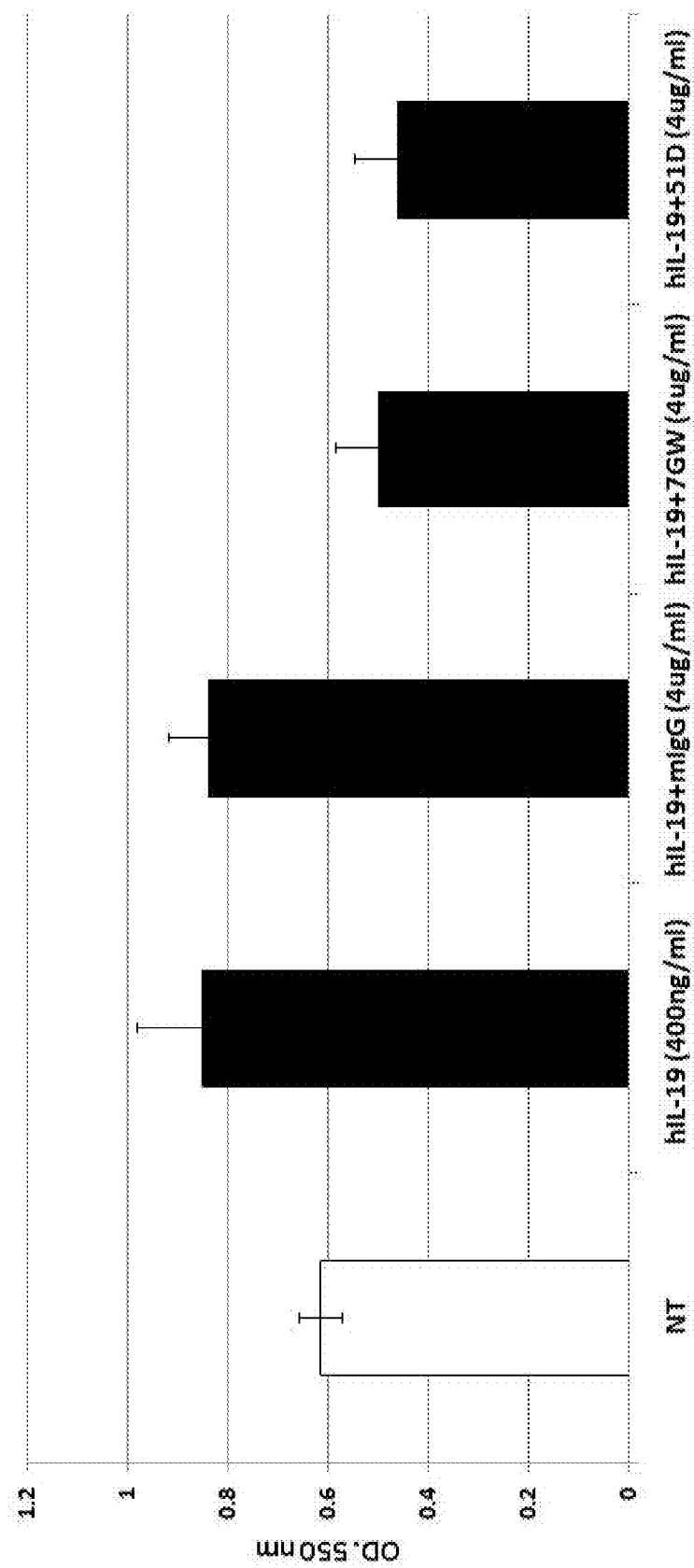

FIG. 6 is a chart showing inhibition of IL-19 induced proliferation of human esophagus cancer cells (CE81T cells) by monoclonal antibodies mAb7GW and mAb51D.

DETAILED DESCRIPTION OF THE INVENTION

Described herein is a method for treating disorders associated with signaling pathways mediated by the IL-20 receptor in a subject using an agent that suppresses IL-20 receptor activity. In some embodiments, the disorders are associated with excessive IL-20 receptor-medicated signaling. Such disorders include, but are not limited to, osteoporosis (including osteoporosis induced by estrogen deficiency, menopause, or inflammation), renal failure (e.g., acute renal failure or chronic kidney disease), diabetic nephropathy, cancer (e.g., oral cancer, esophagus cancer, and breast cancer), rheumatoid arthritis, osteolysis induced by cancer (e.g., breast cancer, prostate cancer, lung cancer, renal cell carcinoma, giant cell tumor of bone, or multiple myeloma with bone metastasis), and ischemic reperfusion (stroke). The term "IL-20 receptor" used herein refers to the dimeric complex formed by IL-20R1 and IL-20R2 subunits. Human IL-20R1 and IL-20R2 subunits are disclosed under GenBank accession numbers NP_055247 (protein)/NM_014432.2 (mRNA) and NP_653318 (protein)/NM_144717 (mRNA), respectively.

An agent that suppresses IL-20 receptor activity can be (i) an antibody that neutralizes IL-20 receptor activity via, e.g., binding to IL-20R1, (ii) an antisense nucleic acid of one of the IL-20 receptor subunit, (iii) a dominant negative mutant of IL-19, IL-20, or IL-24, or (iv) a small molecule that inhibits IL-20 receptor.

(i) IL-20 Receptor Neutralizing Antibodies

An antibody that neutralizes the activity of IL-20 receptor can bind to the receptor (i.e., binds to either the R1 or R2 subunit) and suppress signal transduction mediated by the receptor (e.g., reducing the IL-20 receptor-mediated signaling by at least 20%, 30%, 40%, 50%, 60%, 70%, 80%, 90% or greater) The term "antibody" used herein includes intact immunoglobulin molecules, e.g., IgG, IgA, and IgM, antigen binding fragments thereof, e.g., Fab, F(ab')$_2$, and Fv, and genetically engineered antibody molecules, e.g., chimeric antibody, humanized antibody, scFv (single chain antibody), dAb (domain antibody; see Ward, et. al. (1989) Nature, 341: 544), and bi-specific antibody.

The antibody used in the treatments described herein can be either monoclonal or polyclonal. A "monoclonal antibody" refers to a homogenous antibody population and a "polyclonal antibody" refers to a heterogenous antibody population. These two terms do not limit the source of an antibody or the manner in which it is made.

In one example, the IL-20 receptor-neutralizing antibody is a humanized antibody. A humanized antibody contains a human immunoglobulin (i.e., recipient antibody) in which regions/residues responsible for antigen binding (e.g., the complementarity determining regions, particularly the specificity-determining residues therein) are replaced with those from a non-human immunoglobulin (i.e., donor antibody). Methods to identify regions/residues in the heavy and light chains of an antibody are well known in the art. See, e.g., Almagro, J. Mol. Recognit. 17:132-143 (2004); and Chothia et al., J. Mol. Biol. 227:799-817 (1987). In some instances, one or more residues inside a framework region of the recipient antibody are also replaced with those from the donor antibody. A humanized antibody may also contain residues from neither the recipient antibody nor the donor antibody. These residues are included to further refine and optimize antibody performance.

In some embodiments, the IL-20 receptor-neutralizing antibody is monoclonal antibody mAb7GW or mAb51D, an antigen-binding fragment thereof, or a functional equivalent of either mAb7GW or mAb51D. Shown below are the amino acid sequences of the heavy chains and light chains of mAb7GW and mAb51D, as well as their encoding nucleotide sequences.

```
Heavy Chain of mAb7GW:
Amino Acid Sequence
                                        (SEQ ID NO: 1)
M R V L I L L W L F T A F P G I L S V V Q L Q E S
    Signal peptide

S G P G L V K P S Q S L S L T C T V T G Y S I T S

D Y A W N W I R Q F P G N R L E W M G Y I D Y S G
 CDR1                                        CDR2

S T K Y N P S L K S R I S V T R D T S K N Q F F L

Q L N S V T T E D T A T Y Y C A R D F G D A Y W G
                                      CDR3

Q G T L V T V S A A K T T P P S V Y P L A P G S A

A Q T N S M V T L G C L V K G Y F P E P V T V T W

N S G S L S S G V H T F P A V L Q S D L Y T L S S

S V T V P S S T W P S E T V T C N V A H P A S S T

K V D K K I V P R D C G C K P C I C T V P E V S S

V F I F P P K P K D V L T I T L T P K V T C V V V

D I S K D D P E V Q F S W F V D D V E V H T A Q T

Q P R E E Q F N S T F R S V S E L P I M H Q D W L

N G K E F K C R V N S A A F P A P I E K T I S K T

K G R P K A P Q V Y T I P P P K E Q M A K D K V S

L T C M I T D F F P E D I T V E W Q W N G Q P A E

N Y K N T Q P I M D T D G S Y F V Y S K L N V Q K

S N W E A G N T F T C S V L H E G L H N H H T E K

S L S H S P G K
(The italic region refers to the heavy chain
constant region.)

Nucleotide Sequence
                                        (SEQ ID NO: 2)
ATGAGAGTGCTGATTCTTTTGTGGCTGTTCACAGCCTTTCCTGGTATCC
    Signal peptide

TGTCTGTTGTGCAGCTTCAGGAGTCGGGACCTGGCCTGGTGAAACCTTC

TCAGTCTCTGTCCCTCACCTGCACTGTCACTGGCTACTCAATCACCAGT

GATTATGCCTGGAACTGGATCCGGCAGTTTCCAGGAAACAGACTGGAGT
 CDR1

GGATGGGCTACATAGACTACAGTGGTAGCACTAAATACAACCCCTCTCT
            CDR2
```

CAAAAGTCGAATCTCTGTCACTCGAGACACATCCAAGAACCAGTTCTTC

CTGCAGTTGAATTCTGTGACTACTGAGGACACAGCCACATATTACTGTG

CAAGAGACTTTGGTGATGCTTACTGGGGCCAGGGGACTCTGGTCACTGT
      CDR3

*CTCTGCAGCCAAAACGACACCCCATCTGTCTATCCACTGGCCCCTGGA*

*TCTGCTGCCAAACTAACTCCATGGTGACCCTGGGATGCCTGGTCAAGG*

*GCTATTTCCCTGAGCCAGTGACAGTGACCTGGAACTCTGGATCCCTGTC*

*CAGCGGTGTGCACACCTTCCCAGCTGTCCTGCAGTCTGACCTCTACACT*

*CTGAGCAGCTCAGTGACTGTCCCCTCCAGCACCTGGCCCAGCGAGACCG*

*TCACCTGCAACGTTGCCCACCCGGCCAGCAGCACCAAGGTGGACAAGAA*

*AATTGTGCCCAGGGATTGTGGTTGTAAGCCTTGCATATGTACAGTCCCA*

*GAAGTATCATCTGTCTTCATCTTCCCCCCAAAGCCCAAGGATGTGCTCA*

*CCATTACTCTGACTCCTAAGGTCACGTGTGTTGTGGTAGACATCAGCAA*

*GGATGATCCCGAGGTCCAGTTCAGCTGGTTTGTAGATGATGTGGAGGTG*

*CACACAGCTCAAACGCAACCCCGGAGGAGCAGTTCAACAGCACTTTCC*

*GCTCAGTCAGTGAACTTCCCATCATGCACCAGGACTGGCTCAATGGCAA*

*GGAGTTCAAATGCAGGGTCAACAGTGCAGCTTTCCCTGCCCCCATCGAG*

*AAAACCATCTCCAAAACCAAAGGCAGACCGAAGGCTCCACAGGTGTACA*

*CCATTCCACCTCCCAAGGAGCAAATGGCCAAGGATAAAGTCAGTCTGAC*

*CTGCATGATAACAGACTTCTTCCCTGAAGACATTACTGTGGAGTGGCAG*

*TGGAATGGGCAGCCAGCGGAGAACTACAAGAACACTCAGCCCATCATGG*

*ACACAGATGGCTCTTACTTCGTCTACAGCAAGCTCAATGTGCAGAAGAG*

*CAACTGGGAGGCAGGAAATACTTTCACCTGCTCTGTGTTACATGAGGGC*

*CTGCACAACCACCATACTGAGAAGAGCCTCTCCCACTCTCCTGGTAAAT*

*GA*
(The italic region encodes the heavy chain constant region.)

Light Chain of mAb7GW:
Amino Acid Sequence
(SEQ ID NO: 3)
M D S Q A Q V L M L L L L W V S G S C G D I V M S
    Signal peptide

Q S P S S L A V S V G E K V T M S C K S S Q S L L

Y S R N Q K N Y L A W Y Q L K P G Q S P K L L I Y
CDR1

W A S T R E S G V P D R F T G S G S G T D F T L T
CDR2

I S S V K A E D L A V Y Y C Q Q Y Y S Y P L T F G
                            CDR3

A G T K L E L K R *A D A A P T V S I F P P S S E Q*

*L T S G G A S V V C F L N N F Y P K D I N V K W K*

*I D G S E R Q N G V L N S W T D Q D S K D S T Y S*

*M S S T L T L T K D E Y E R H N S Y T C E A T H K*

*T S T S P I V K S F N R N E C*
(The italic region refers to the light chain constant region.)

Nucleotide Sequence
(SEQ ID NO: 4)
ATGGATTCACAGGCCCAGGTTCTTATGTTACTGCTGCTATGGGTATCTG
    Signal peptide

GTTCCTGTGGGGACATTGTGATGTCACAGTCTCCATCCTCCCTAGCTGT

GTCAGTTGGAGAGAAGGTTACTATGAGCTGCAAGTCCAGTCAGAGCCTT

TTATATAGTAGGAATCAAAAGAACTACTTGGCCTGGTACCAGCTGAAGC
CDR1

CAGGGCAGTCTCCTAAACTGCTGATTTACTGGGCATCCACTAGGGAATC
                               CDR2

TGGGGTCCCTGATCGCTTCACAGGCAGTGGATCTGGGACAGATTTCACT

CTCACCATCAGCAGTGTGAAGGCTGAAGACCTGGCAGTTTATTACTGTC

AGCAATATTATAGCTATCCGCTCACGTTCGGTGCTGGGACCAAGCTGGA
CDR3

GCTGAAACGGGCTGATGCTGCACCAACTGTATCCATCTTCCCACCATCC

AGTGAGCAGTTAACATCTGGAGGTGCCTCAGTCGTGTGCTTCTTGAACA

ACTTCTACCCCAAAGACATCAATGTCAAGTGGAAGATTGATGGCAGTGA

GAACGACAAAATGGCGTCCTGAACAGTTGGACTGATCAGGACAGCAAAG

ACAGCACCTACAGCATGAGCAGCACCCTCACGTTGACCAAGGACGAGTA

TGAACGACATAACAGCTATACCTGTGAGGCCACTCACAAGACATCAACT

TCACCCATTGTCAAGAGCTTCAACAGGAATGAGTGTTAG
(The italic region encodes the light chain constant region.)

Heavy Chain of mAb51D:
Amino Acid Sequence
(SEQ ID NO: 5)
M N F G L S L I F L A L I L K G V Q C EVQLVEAGGDLVKPGGSLKLSCAASGFSLS
    Signal peptide

NYGMSWVRQTPDKRLEWVASISSGGRFTSYPDSVRGRFTISRDNAKNTL
CDR1                 CDR2

YLQMSGLKSEDTAMYYCARHDGNGGDYWGQGTSVTVSS*AKTTPPSVYPL*
                    CDR3

*APGSAAQTNSMVTLGCLVKGYFPEPVTVTWNSGSLSSGVHTFPAVLQSD*

*LYTLSSSVTVPSSTWPSETVTCNVAHPASSTKVDKKIVPRDCGCKPCIC*

*TVPEVSSVFIFPPKPKDVLTITLTPKVTCVVVDISKDDPEVQFSWFVDD*

*VEVHTAQTQPREEQFNSTFRSVSELPIMHQDWLNGKEFKCRVNSAAFPA*

*PIEKTISKTKGRPKAPQVYTIPPPKEQMAKDKVSLTCMITDFFPEDITV*

*EWQWNGQPAENYKNTQPIMDTDGSYFVYSKLNVQKSNWEAGNTFTCSVL*

*HEGLHNHHTEKSLSHSPGK*
(The italic region refers to the heavy chain constant region.)

Nucleotide Sequence
(SEQ ID NO: 6)
ATGAACTTCGGGCTCAGCCTGATTTTCCTTGCCCTCATTTTAAAAGGTG
    Signal peptide

TCCAGTGTGAGGTGCAGCTGGTGGAGGCTGGGGGAGACTTAGTGAAGCC

TGGAGGGTCCCTGAAACTCTCCTGTGCGGCCTCTGGATTCAGTTTGAGT

AACTATGGCATGTCCTGGGTTCGCCAGACTCCAGACAAGAGGCTGGAGT
CDR1

GGGTCGCAAGCATTAGTAGTGGTGGTCGTTTCACCTCCTATCCAGACAG
         CDR2

-continued

```
TGTGAGGGGGCGATTCACCATCTCCAGAGACAATGCCAAGAACACCCTG

TACCTGCAAATGAGCGGTCTGAAGTCTGAGGACACAGCCATGTATTACT

GTGCAAGACACGACGGCAACGGTGGGGACTACTGGGGTCAAGGAACCTC
              CDR3

AGTCACCGTCTCCTCAGCCAAAACGACACCCCCATCTGTCTATCCACTG

GCCCCTGGATCTGCTGCCCAAACTAACTCCATGGTGACCCTGGGATGCC

TGGTCAAGGGCTATTTCCCTGAGCCAGTGACAGTGACCTGGAACTCTGG

ATCCCTGTCCAGCGGTGTGCACACCTTCCCAGCTGTCCTGCAGTCTGAC

CTCTACACTCTGAGCAGCTCAGTGACTGTCCCCTCCAGCACCTGGCCCA

GCGAGACCGTCACCTGCAACGTTGCCCACCCGGCCAGCAGCACCAAGGT

GGACAAGAAAATTGTGCCCAGGGATTGTGGTTGTAAGCCTTGCATATGT

ACAGTCCCAGAAGTATCATCTGTCTTCATCTTCCCCCCAAAGCCCAAGG

ATGTGCTCACCATTACTCTGACTCCTAAGGTCACGTGTGTTGTGGTAGA

CATCAGCAAGGATGATCCCGAGGTCCAGTTCAGCTGGTTTGTAGATGAT

GTGGAGGTGCACACAGCTCAGACGCAACCCCGGGAGGAGCAGTTCAACA

GCACTTTCCGCTCAGTCAGTGAACTTCCCATCATGCACCAGGACTGGCT

CAATGGCAAGGAGTTCAAATGCAGGGTCAACAGTGCAGCTTTCCCTGCC

CCCATCGAGAAAACCATCTCCAAAACCAAAGGCAGACCGAAGGCTCCAC

AGGTGTACACCATTCCACCTCCCAAGGAGCAGATGGCAAGGATAAAGT

CAGTCTGACCTGCATGATAACAGACTTCTTCCCTGAAGACATTACTGTG

GAGTGGCAGTGGAATGGGCAGCCAGCGGAGAACTACAAGAACACTCAGC

CCATCATGGACACAGATGGCTCTTACTTCGTCTACAGCAAGCTCAATGT

GCAGAAGAGCAACTGGGAGGCAGGAAATACTTTCACCTGCTCTGTGTTA

CATGAGGGCCTGCACAACCACCATACTGAGAAGAGCCTCTCCCACTCTC

CTGGTAAATGA
(The italic region encodes the heavy chain
constant region.)

Light Chain of mAb51D:
Amino Acid Sequence
                                       (SEQ ID NO: 7)
MDFQVQIFSFLLISASVIMSRGQIVLSQFPAILSASPGEKVTMTCRA
    Signal peptide

RSSVSFMHWYQQKPGSSPKPWIYATSNLASGVPPRFSGSGSGTSYSLTI
CDR1                    CDR2

SRVEAEDAATYYCQQWSSNPYTFGGGTKLEIKRADAAPTVSIFPPSSEQ
              CDR3

LTSGGASVVCFLNNFYPKDINVKWKIDGSERQNGVLNSWTDQDSKDSTY

SMSSTLTLTKDEYERHNSYTCEATHKTSTSPIVKSFNRNEC
(The italic region refers to the light chain
constant region)

Nucleotide Sequence
                                       (SEQ ID NO: 8)
ATGGATTTTCAAGTGCAGATTTTCAGCTTCCTGCTAATCAGTGCTTCA
                Signal peptide

GTCATAATGTCCAGAGGACAAATTGTTCTCTCCCAGTTTCCAGCAATC

CTGTCTGCATCTCCAGGGGAGAAGGTCACAATGACTTGCAGGGCCAGG

TCAAGTGTAAGTTTCATGCACTGGTACCAGCAGAAGCCAGGATCCTCC
CDR1

CCCAAACCCTGGATTTATGCCACATCCAACCTGGCTTCTGGAGTCCCT
                       CDR2

CCTCGCTTCAGTGGCAGTGGGTCTGGGACCTCTTACTCTCTCACAATC

AGCAGAGTGGAGGCTGAAGATGCTGCCACTTATTACTGCCAGCAGTGG

AGTAGTAACCCATACACGTTCGGAGGGGGGACTAAGCTGGAAATAAAA
CDR3

CGGGCTGATGCTGCACCAACTGTATCCATCTTCCCACCATCCAGTGAG

CAGTTAACATCTGGAGGTGCCTCAGTCGTGTGCTTCTTGAACAACTTC

TACCCCAAAGACATCAATGTCAAGTGGAAGATTGATGGCAGTGAACGA

CAAAATGGCGTCCTGAACAGTTGGACTGATCAGGACAGCAAAGACAGC

ACCTACAGCATGAGCAGCACCCTCACGTTGACCAAGGACGAGTATGAA

CGACATAACAGCTATACCTGTGAGGCCACTCACAAGACATCAACTTCA

CCCATTGTCAAGAGCTTCAACAGGAATGAGTGTTAG
(The italic region encodes the light chain
constant region.)
```

A functional equivalent of mAb7GW or mAb51D has the same epitope-binding specificity as mAb7GW or mAb51D and exhibits at least 20% (e.g., 30%, 40%, 50%, 60%, 70%, 80%, 90%, or greater) of the activity of neutralizing IL-20 receptor as relative to mAb7GW or mAb51D. In some embodiments, a functional equivalent of mAb7GW or mAb51D contains the same regions/residues responsible for antigen-binding as mAb7GW or mAb51D, such as the same specificity-determining residues in the CDRs or the whole CDRs. The regions/residues that are responsible for antigen-binding can be identified from amino acid sequences of the heavy chain/light chain sequences of mAb7GW or mAb51D (shown above) by methods known in the art. See, e.g., www.bioinf.org.uk/abs; Almagro, J. Mol. Recognit. 17:132-143 (2004); and Chothia et al., J. Mol. Biol. 227:799-817 (1987). A functional equivalent of mAb7GW or mAb51D can be a genetically engineered antibody derived from one of the monoclonal antibodies (e.g., chimeric, single-chain, or humanized).

In another example, the IL-20 receptor neutralizing antibody is a bi-specific antibody capable of binding to both IL-20R1 and one of IL-19 and IL-20. Such a bi-specific antibody contains two heavy chain-light chain pairs, one pair binding to IL-20R1 and the other pair binding to one of the cytokines.

Methods of making monoclonal and polyclonal antibodies and fragments thereof in animals are well known in the art. See, for example, Harlow and Lane, (1988) Antibodies: A Laboratory Manual, Cold Spring Harbor Laboratory, New York.

In general, to produce antibodies against a protein (e.g., IL-20R1 or IL-20R2), the protein or a fragment thereof, optionally coupled to a carrier protein, such as KLH, can be mixed with an adjuvant, and injected into a host animal. Antibodies produced in the animal can then be purified by peptide affinity chromatography. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, CpG, surface-active substances such as lysolecithin, pluronic polyols, polyanions, peptides, oil emulsions, keyhole limpet hemocyanin, and dinitrophenol. Useful human adjuvants include BCG (bacille Calmette-Guerin) and *Corynebacterium parvum*.

Polyclonal antibodies are present in the sera of the immunized subjects. Monoclonal antibodies can be prepared using standard hybridoma technology (see, for example, Kohler et al. (1975) Nature 256, 495; Kohler et al. (1976) Eur. J. Immunol. 6, 511; Kohler et al. (1976) Eur J Immunol 6, 292; and Hammerling et al. (1981) Monoclonal Antibodies and T Cell Hybridomas, Elsevier, N.Y.). In particular, monoclonal antibodies can be obtained by any technique that provides for the production of antibody molecules by continuous cell lines in culture such as described in Kohler et al. (1975) Nature 256, 495 and U.S. Pat. No. 4,376,110; the human B-cell hybridoma technique (Kosbor et al. (1983) Immunol Today 4, 72; Cole et al. (1983) Proc. Natl. Acad. Sci. USA 80, 2026, and the EBV-hybridoma technique (Cole et al. (1983) Monoclonal Antibodies and Cancer Therapy, Alan R. Liss, Inc., pp. 77-96). Such antibodies can be of any immunoglobulin class including IgG, IgM, IgE, IgA, IgD, and any subclass thereof. The hybridoma producing the monoclonal antibodies disclosed herein may be cultivated in vitro or in vivo. The ability to produce high titers of monoclonal antibodies in vivo makes it a particularly useful method of production.

After obtaining antibodies specific to either IL-20R1 or IL-20R2, their ability to neutralize IL-20 receptor can be determined by a routine procedure. For example, the level of IL-10 secretion induced by IL-19 in peripheral blood mononuclear cells is used as an indicator of IL-20 receptor activity. See Example 1 below. In an example, IL-20 receptor activity is determined by examining IL-19-induced caspase 3 and caspase 9 cleavage in renal epithelial cells. Antibodies that specifically binding to IL-20 receptor and suppressing its activity (i.e., neutralizing IL-20 receptor) are selected for use in the methods disclosed herein.

Antigen-binding fragments of the just-mentioned IL-20 receptor neutralizing antibody can be prepared via routine methods. For example, F(ab')$_2$ fragments can be produced by pepsin digestion of an antibody molecule, and Fab fragments that can be generated by reducing the disulfide bridges of F(ab')$_2$ fragments.

The IL-20 receptor neutralizing antibody can also be used as a basis for preparing genetically engineered antibodies, including chimeric antibody, humanized antibody, and single-chain antibody. Techniques developed for the production of "chimeric antibodies" can be used. See, e.g., Morrison et al. (1984) Proc. Natl. Acad. Sci. USA 81, 6851; Neuberger et al. (1984) Nature 312, 604; and Takeda et al. (1984) Nature 314:452. A chimeric antibody is a molecule in which different portions are derived from different animal species, such as those having a variable region derived from a murine monoclonal antibody and a human immunoglobulin constant region. Antibodies can also be humanized by methods known in the art. For example, monoclonal antibodies with a desired binding specificity can be commercially humanized.

Fully human antibodies, such as those expressed in transgenic animals are also features of this disclosure (see, e.g., Green et al. (1994) Nature Genetics 7, 13; and U.S. Pat. Nos. 5,545,806 and 5,569,825). Alternatively, fully human antibodies can be obtained by screening a human antibody library (e.g., a phage display or yeast display library) against an antigen (e.g., IL-20R1).

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704,692) can be adapted to produce a phage scFv library and scFv clones specific to IL-20R1 or IL-20R2 can be identified from the library following routine procedures. Positive clones can be subjected to further screening to identify those that suppress IL-20 receptor activity.

(ii) Antisense Nucleic Acid of IL-20 Receptor

An antisense nucleic acid of IL-20 receptor, DNA or RNA, is an oligonucleotide capable of forming base-pairs with the IL-20R1 or IL-20R2 gene (either the sense chain or the antisense chain), thereby suppressing its expression. Preferably, the oligonucleotide has a maximum length of 150 (e.g., 100, 80, 60, or 40) nucleotides.

The antisense nucleic acid can be a double-strand RNA (dsRNA) that inhibits the expression of IL-20R1 or IL-20R2 via RNA interference. RNA interference (RNAi) is a process in which a dsRNA directs homologous sequence-specific degradation of messenger RNA. In mammalian cells, RNAi can be triggered by 21-nucleotide duplexes of small interfering RNA (siRNA) without activating the host interferon response. The dsRNA used in the methods disclosed herein can be a siRNA (containing two separate and complementary RNA chains) or a short hairpin RNA (i.e., a RNA chain forming a tight hairpin structure), both of which can be designed based on the sequence of the target gene. Alternatively, it can be a microRNA.

Preferably, an antisense nucleic acid as described above contains non-naturally-occurring nucleobases, sugars, or covalent internucleoside linkages (backbones). Such a modified oligonucleotide confers desirable properties such as enhanced cellular uptake, improved affinity to the target nucleic acid, and increased in vivo stability.

In one example, the antisense nucleic acid has a modified backbone, including those that retain a phosphorus atom (see, e.g., U.S. Pat. Nos. 3,687,808; 4,469,863; 5,321,131; 5,399,676; and 5,625,050) and those that do not have a phosphorus atom (see, e.g., U.S. Pat. Nos. 5,034,506; 5,166,315; and 5,792,608). Examples of phosphorus-containing modified backbones include, but are not limited to, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having 3'-5' linkages, or 2'-5' linkages. Such backbones also include those having inverted polarity, i.e., 3' to 3', 5' to 5' or 2' to 2' linkage. Modified backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In another example, the antisense nucleic acid used in the disclosed methods includes one or more substituted sugar moieties. Such substituted sugar moieties can include one of the following groups at their 2' position: OH; F; O-alkyl, S-alkyl, N-alkyl, O-alkenyl, S-alkenyl, N-alkenyl; O— alkynyl, S-alkynyl, N-alkynyl, and O-alkyl-O-alkyl. In these groups, the alkyl, alkenyl and alkynyl can be substituted or unsubstituted $C_1$ to $C_{10}$ alkyl or $C_2$ to $C_{10}$ alkenyl and alkynyl. They may also include at their 2' position heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide. Preferred substituted sugar moieties include those having 2'-methoxyethoxy, 2'-dimethylaminooxyethoxy, and 2'-dimethylaminoethoxyethoxy. See Martin et al., Helv. Chim. Acta, 1995, 78, 486-504.

In yet another example, the antisense nucleic acid includes one or more modified native nucleobases (i.e., adenine, guanine, thymine, cytosine and uracil). Modified nucleobases include those described in U.S. Pat. No. 3,687,808, The Concise Encyclopedia Of Polymer Science And Engineering, pages 858-859, Kroschwitz, J. I., ed. John Wiley & Sons, 1990, Englisch et al., Angewandte Chemie, International Edition, 1991, 30, 613, and Sanghvi, Y. S., Chapter 15, Antisense Research and Applications, pages 289-302, CRC Press, 1993. Certain of these nucleobases are particularly useful for increasing the binding affinity of the antisense oligonucleotide to its target nucleic acid. These include 5-substituted pyrimidines, 6-azapyrimidines and N-2, N-6 and O-6 substituted purines (e.g., 2-aminopropyl-adenine, 5-propynyluracil and 5-propynylcytosine). See Sanghvi, et al., eds., Antisense Research and Applications, CRC Press, Boca Raton, 1993, pp. 276-278).

Any of the antisense nucleic acids can be synthesized by methods known in the art. See, e.g., Caruthers et al., 1992, Methods in Enzymology 211, 3-19, Wincott et al., 1995, Nucleic Acids Res. 23, 2677-2684, Wincott et al., 1997, Methods Mol. Bio. 74, 59, Brennan et al., 1998, Biotechnol Bioeng., 61, 33-45, and Brennan, U.S. Pat. No. 6,001,311. It can also be transcribed from an expression vector and isolated using standard techniques.

(iii) Dominant Negative Mutant of IL-19, IL-20, or IL-24

A dominant negative mutant of IL-19, IL-20, or IL-24 retains the receptor binding activity of its wild-type counterpart but has reduced or no ability to activate IL-20 receptor. In some embodiments, the dominant negative mutant has at least 10%, 20%, 30%, 40%, 50%, 60%, 70%, 80%, or 90% lower activity to activate the IL-20 receptor as compared with its wild-type counterpart. Thus, such a mutant is capable of blocking the signaling pathway triggered by binding of IL-19, IL-20, or IL-24 to the receptor. Typically, the mutant shares at least 70% (e.g., 80%, 85%, 90%, and 95%) sequence identity to the wild-type cytokine.

The "percent identity" of two amino acid sequences is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., *Nucleic Acids Res.* 25 (17):3389-3402, 1997. When utilizing BLAST and Gapped BLAST programs, the default parameters of the respective programs (e.g., XBLAST and NBLAST) can be used.

The dominant negative mutant described above can be prepared by introducing one or more mutations at a position(s) in IL-19 (e.g., GenBank accession number AF453946; 16 Oct. 2002), IL-20 (e.g., GenBank accession number AF224266, 24 Jan. 2001, or NM_018724, 5 Apr. 2010), or IL-24 (e.g., GenBank accession number BC009681, 6 Apr. 2010) that is responsible for receptor activation.

(iv) Small Molecule Inhibiting IL-20 Receptor

A small molecule that inhibits IL-20 receptor activity typically has a maximum molecule weight of 2,000 kDa. Such a small molecule can be screened by any method known in the art. One representative example follows. Cells displaying IL-20 receptor are incubated with a test compound in the presence of IL-19, IL-20, or IL-24 under suitable conditions allowing cytokine-receptor binding. After a suitable period, the culture medium is collected and examined to determine the level of a molecule inducible by binding of the cytokine to the receptor, e.g., IL-10 in response to IL-19 or TNF-alpha in response to IL-20. A decrease in the secretion level of the molecule in the presence of a test compound indicates that the compound inhibits IL-20 receptor activity.

The above-mentioned small molecule can be obtained from compound libraries. The libraries can be spatially addressable parallel solid phase or solution phase libraries. See, e.g., Zuckermann et al. J. Med. Chem. 37, 2678-2685, 1994; and Lam Anticancer Drug Des. 12:145, 1997. Methods for the synthesis of compound libraries are well known in the art, e.g., DeWitt et al. PNAS USA 90:6909, 1993; Erb et al. PNAS USA 91:11422, 1994; Zuckermann et al. J. Med. Chem. 37:2678, 1994; Cho et al. Science 261:1303, 1993; Carrell et al. Angew Chem. Int. Ed. Engl. 33:2059, 1994; Carell et al. Angew Chem. Int. Ed. Engl. 33:2061, 1994; and Gallop et al. J. Med. Chem. 37:1233, 1994. Libraries of compounds may be presented in solution (e.g., Houghten Biotechniques 13:412-421, 1992), or on beads (Lam Nature 354:82-84, 1991), chips (Fodor Nature 364:555-556, 1993), bacteria (U.S. Pat. No. 5,223,409), spores (U.S. Pat. No. 5,223,409), plasmids (Cull et al. PNAS USA 89:1865-1869, 1992), or phages (Scott and Smith Science 249:386-390, 1990; Devlin Science 249:404-406, 1990; Cwirla et al. PNAS USA 87:6378-6382, 1990; Felici J. Mol. Biol. 222:301-310, 1991; and U.S. Pat. No. 5,223,409).

One or more of the above-described agents can be mixed with a pharmaceutically acceptable carrier to form a pharmaceutical composition for use in treating osteoporosis, renal failure, or diabetic nephropathy in a subject in need (e.g., a human patient suffering from any of the three diseases). "Acceptable" means that the carrier must be compatible with the active ingredient of the composition (and preferably, capable of stabilizing the active ingredient) and not deleterious to the subject to be treated. Suitable carriers include microcrystalline cellulose, mannitol, glucose, defatted milk powder, polyvinylpyrrolidone, and starch, or a combination thereof.

To practice a treatment disclosed herein, an effective amount of the pharmaceutical composition noted above can be administered to a subject (e.g., a human) in need of the treatment via a suitable route. A human subject who needs the treatment may be a human patient having, at risk for, or suspected of having a disorder associated with the signaling pathway mediated by IL-20 receptor. Such a patient can be identified by routine medical examination.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

In some embodiments, the agent that suppress IL-20 receptor activity is administered to a subject in need of the treatment at an amount sufficient to reduce the level of the IL-20 receptor-mediated signaling by at least 20% (e.g., 30%, 40%, 50%, 60%, 70%, 80%, 90% or greater).

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethylormamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

When an antisense nucleic acid of IL-20 receptor is used, the nucleic acid or a vector expressing it can be delivered to a subject by methods, such as that described in Akhtar et al., 1992, Trends Cell Bio. 2, 139. For example, it can be introduced into cells using liposomes, hydrogels, cyclodextrins, biodegradable nanocapsules, or bioadhesive microspheres. Alternatively, the nucleic acid or vector can be locally delivered by direct injection or by use of an infusion pump. Other approaches include employing various transport and carrier systems, for example through the use of conjugates and biodegradable polymers.

To facilitate delivery, any of the IL-20 receptor suppressing agents can be conjugated with a chaperon agent. As used herein, "conjugated" means two entities are associated, preferably with sufficient affinity that the therapeutic benefit of the association between the two entities is realized. Conjugated includes covalent or noncovalent bonding as well as other forms of association, such as entrapment of one entity on or within the other, or of either or both entities on or within a third entity (e.g., a micelle).

The chaperon agent can be a naturally occurring substance, such as a protein (e.g., human serum albumin, low-density lipoprotein, or globulin), carbohydrate (e.g., a dextran, pullulan, chitin, chitosan, inulin, cyclodextrin or hyaluronic acid), or lipid. It can also be a recombinant or synthetic molecule, such as a synthetic polymer, e.g., a synthetic polyamino acid. Examples of polyamino acids include polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl) methacrylamide copolymer (HMPA), polyethylene glycol (PEG), polyvinyl alcohol (PVA), polyurethane, poly(2-ethylacryllic acid), N-isopropylacrylamide polymers, and polyphosphazine.

In one example, the chaperon agent is a micelle, liposome, nanoparticle, or microsphere, in which the oligonucleotide/interfering RNA is encapsulated. Methods for preparing such a micelle, liposome, nanoparticle, or microsphere are well known in the art. See, e.g., U.S. Pat. Nos. 5,108,921; 5,354,844; 5,416,016; and 5,527,5285.

In another example, the chaperon agent serves as a substrate for attachment of one or more of a fusogenic or condensing agent.

A fusogenic agent is responsive to the local pH. For instance, upon encountering the pH within an endosome, it can cause a physical change in its immediate environment, e.g., a change in osmotic properties which disrupts or increases the permeability of the endosome membrane, thereby facilitating release of the antisense oligonucleotide into host cell's cytoplasm. A preferred fusogenic agent changes charge, e.g., becomes protonated at a pH lower than a physiological range (e.g., at pH 4.5-6.5). Fusogenic agents can be molecules containing an amino group capable of undergoing a change of charge (e.g., protonation) when exposed to a specific pH range. Such fusogenic agents include polymers having polyamino chains (e.g., polyethyleneimine) and membrane disruptive agents (e.g., mellittin). Other examples include polyhistidine, polyimidazole, polypyridine, polypropyleneimine, and a polyacetal substance (e.g., a cationic polyacetal).

A condensing agent interacts with the antisense oligonucleotide, causing it to condense (e.g., reduce the size of the oligonucleotide), thus protecting it against degradation. Preferably, the condensing agent includes a moiety (e.g., a charged moiety) that interacts with the oligonucleotide via, e.g., ionic interactions. Examples of condensing agents include polylysine, spermine, spermidine, polyamine or quarternary salt thereof, pseudopeptide-polyamine, peptidomimetic polyamine, dendrimer polyamine, arginine, amidine, protamine, cationic lipid, cationic porphyrin, and alpha helical peptide.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLE 1

Reduced Osteoporotic Bone Loss in IL-20R1 Knockout Mice

To generate an IL-20R1 knockout mouse, the exon 2 in mouse IL-20R1 gene was deleted via the traditional homologous recombination technology. The deletion of exon 2 was confirmed by Southernblot using a DNA probe hybridizable to the 3' end of exon 2.

Lung tissues from IL-20R1 wild-type (+/+), heterozygote (+/−), and knockout (−/−) mice were examined by co-immunoprecipitation analysis to determine their expression of IL-20 receptor. Briefly, lysates of the lung tissues were incubated with His-tagged IL-20 under suitable conditions that allow IL-20/IL-20 receptor binding. The lysates were then incubated with an anti-His-tag antibody and the resultant pellets were analyzed by immunoblotting to detect presence/absence of IL-20, IL-20R1, IL-20R2, and IL-22R1, using antibodies specific to these proteins. No IL-20R1 protein was detected in the lung lysates from IL-20R1$^{-/-}$ mice, indicating that the IL-20R1$^{-/-}$ mice do not express IL-20R1.

IL-19, which only binds to IL-20R1/IL-20R2 receptor heterodimer, was used to confirm that cells isolated from the IL-20R1$^{-/-}$ mice did not have functional IL-20R1 proteins. Binding of IL-19 to the dimeric receptor stimulates IL-10 expression.

Figure 1:
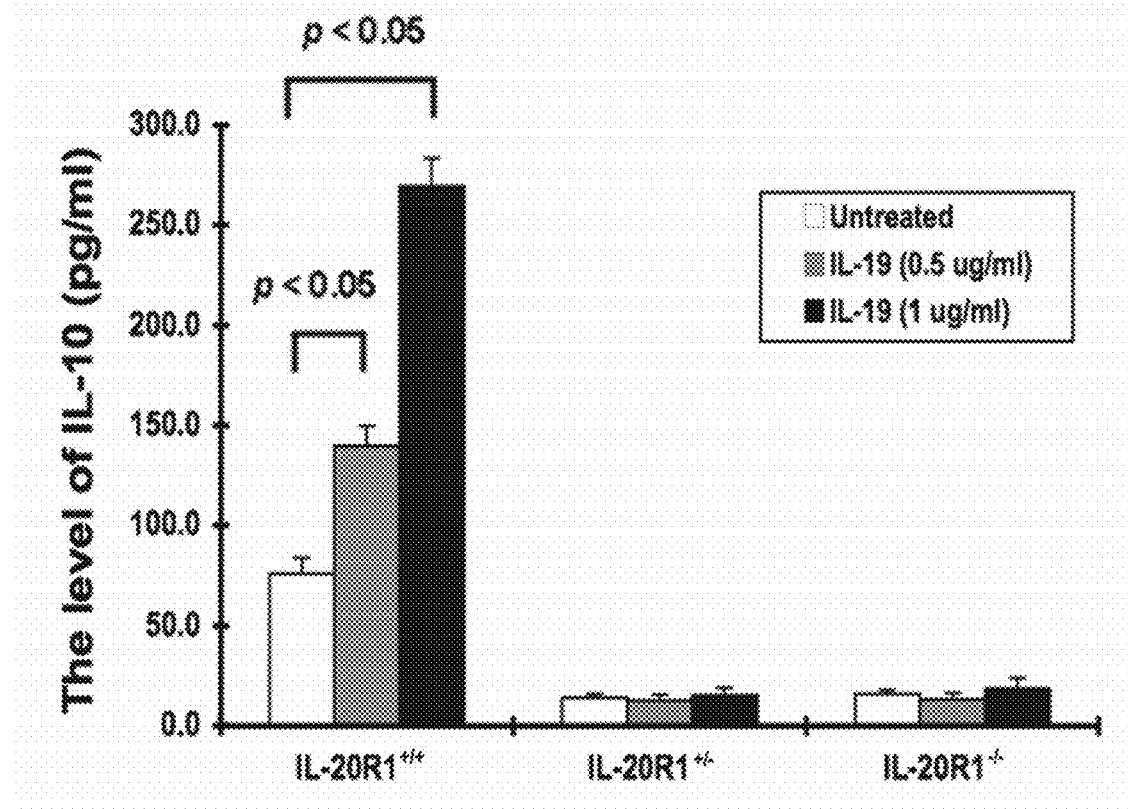
FIG. 1 is a chart showing induction of IL-10 in peripheral blood mononuclear cells from IL-20R1$^{+/+}$, IL-20R1$^{+/-}$, and IL-20R1$^{-/-}$ mice.

Peripheral blood mononuclear cells (PBMCs) were prepared from IL-20R1$^{+/+}$, IL-20R1$^{+/-}$, and IL-20R1$^{-/-}$ mice and treated with IL-19. The levels of IL-10 secreted by the treated cells were determined by ELISA. The results obtained from this study show that IL-10 induction was observed in cells isolated from IL-20R1$^{+/+}$ mice, but not in cells isolated from both IL-20R1$^{+/-}$ and IL-20R1$^{-/-}$ mice. See FIG. 1. This demonstrates that no functional IL-20 receptor were expressed in IL-20R1$^{-/-}$ mice.

Figure 2:
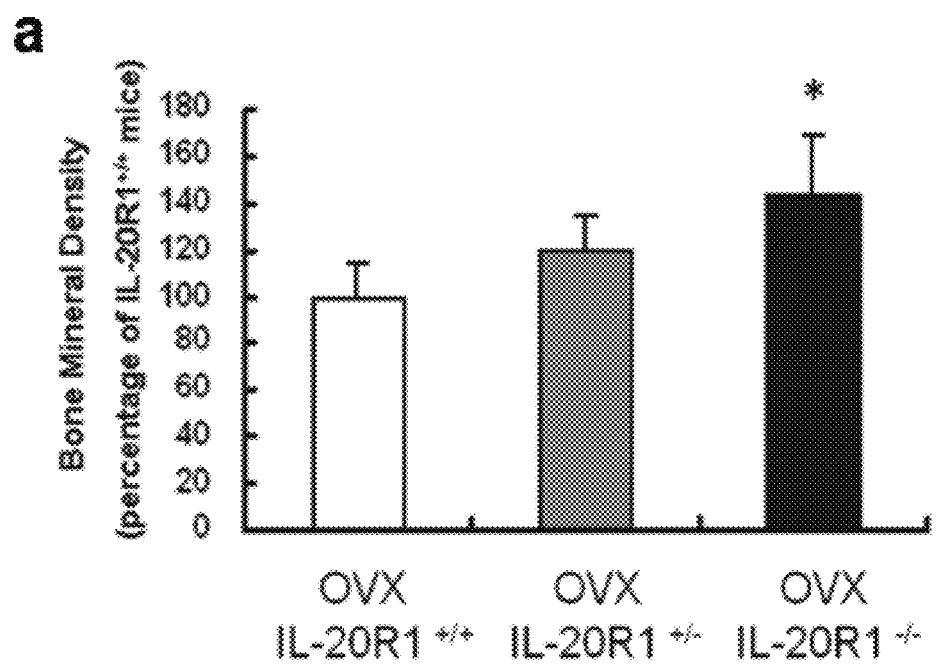
FIG. 2 is a diagram showing OVX-induced osteoporotic bone loss in IL-20R1$^{+/+}$, IL-20R1$^{+/-}$, and IL-20R1$^{-/-}$ mice. Panel a: Bone mineral density in the tibias of OVX mice (n=5 for each type of the mice). Panel b: Osteoclast numbers per bone surface in TRAP-stained sections. (n=5 for each type of the mice). Values are means±standard deviation. Data are representative of 3 independent experiments.
Figure 2:
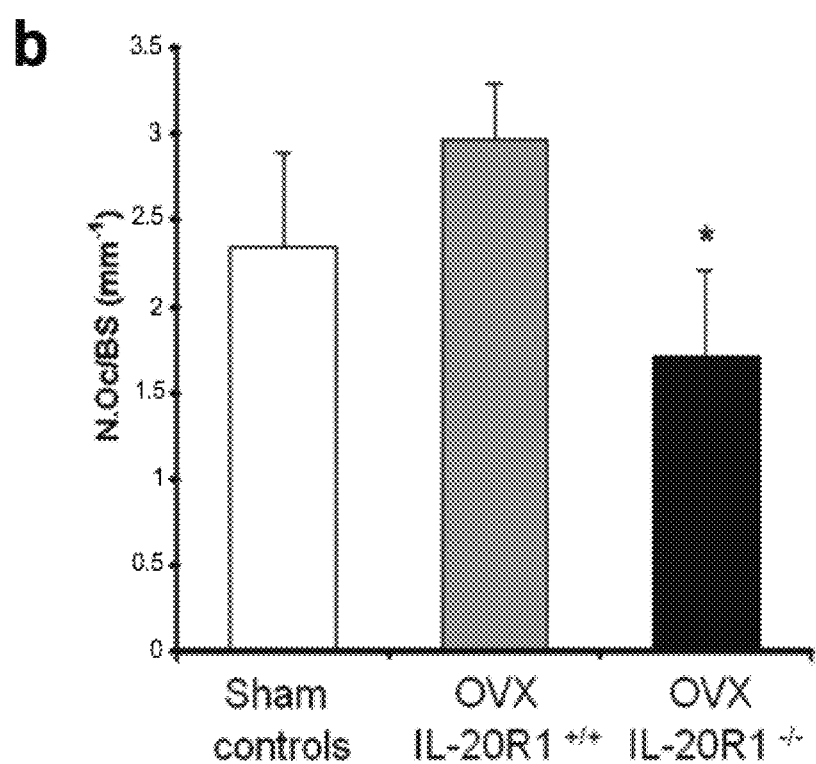

To examine the impact of IL-20R1 deficiency on osteoporosis development, IL-20R1$^{+/+}$, IL-20R1$^{+/-}$, and IL-20R1$^{-/-}$ mice were subjected to dorsal ovariectomization under general anesthesia using pentobarbital (50 mg/kg body weight; Sigma-Aldrich, St. Louis, Mo.) to induce postmenopausal osteoporosis. The ovariectomized mice (OVX mice) were examined by micro-CT analysis to determine their bone mineral density. The bone mineral density of the OVX IL-20R1$^{-/-}$ mice was much higher than that in the OVX IL-20R1$^{+/+}$ mice. See FIG. 2, panel a. (P<0.05). In addition, the osteoclast numbers (OC) were significantly reduced in the IL-20R1$^{-/-}$ mice as compared to those in the IL-20R1$^{+/+}$ mice. See FIG. 2, panel b. Analysis of bone histomorphometric parameters showed that ovariectomization caused a significant decrease in bone volume (BV/TV, %), trabecular bone thickness (Tb. Th, μm), and trabecular number (Tb. N, 1/mm) in the OVX IL-20R1$^{+/+}$ mice relative to those in the OVX-IL-20R1$^{-/-}$ mice. OVX-IL-20R1$^{-/-}$ mice also showed a level of trabecular separation (Tb. Sp, μm) lower than that in the OVX-IL-20R1$^{+/+}$ mice (P<0.05). The results showed that eliminating IL-20 receptor activity by knocking out IL-20R1 protected mice from developing osteoporosis.

EXAMPLE 2

Reduced Severity of HgCl$_2$-Induced Renal Failure in IL-20R1 Knockout Mice

The IL-20R1$^{+/+}$, IL-20R1$^{+/-}$, and IL-20R1$^{-/-}$ mice mentioned above were subjected to HgCl$_2$ treatment to induce acute renal failure (ARF), following the method described in Li H H, et al., *Genes Immun.* 2008 July; 9 (5):395-404.

Figure 3:
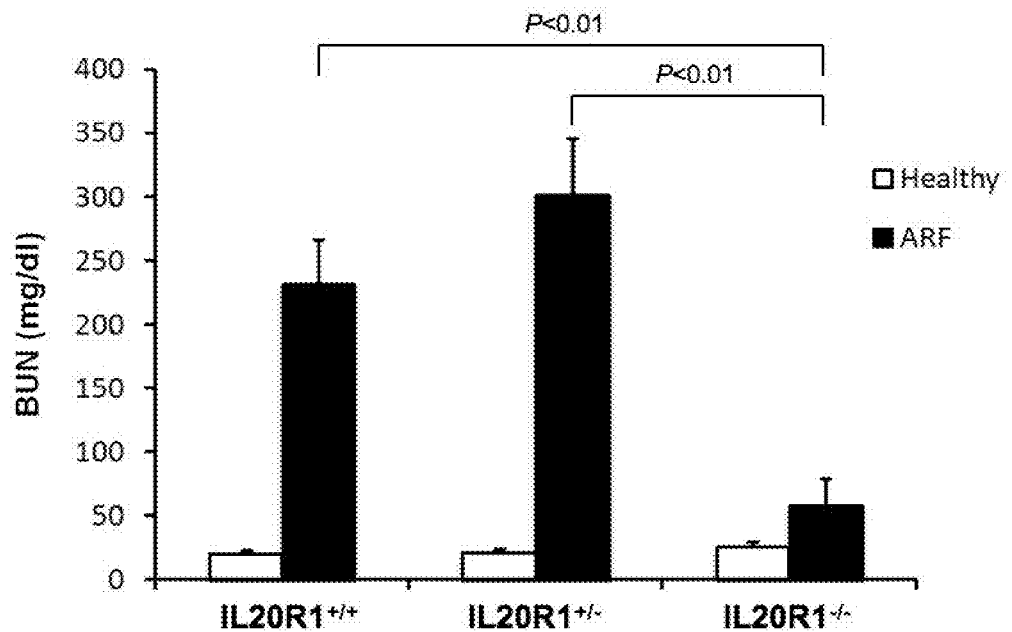
FIG. 3 is a diagram showing renal failure severity in IL-20R1$^{+/+}$, IL-20R1$^{+/-}$, and IL-20R1$^{-/-}$ mice. Panel A: Serum BUN levels of HgCl$_2$-treated IL-20R1$^{+/+}$ (n=5), IL-20R1$^{+/-}$ (n=5), and IL-20R1$^{-/-}$ (n=5) mice were analyzed at day 3. Values are means±standard error mean. P<0.01 compared with IL-20R1$^{+/+}$ mice. Panel B: Quantitative analysis of the area of damaged tubular cells from IL-20R1$^{+/+}$ (n=5), IL-20R1$^{+/-}$ (n=5), and IL-20R1$^{-/-}$ (n=5) mice treated with HgCl$_2$ after 4 days. Values are means±standard error mean. *P<0.05 compared with IL-20R1$^{+/+}$ mice.
Figure 3:
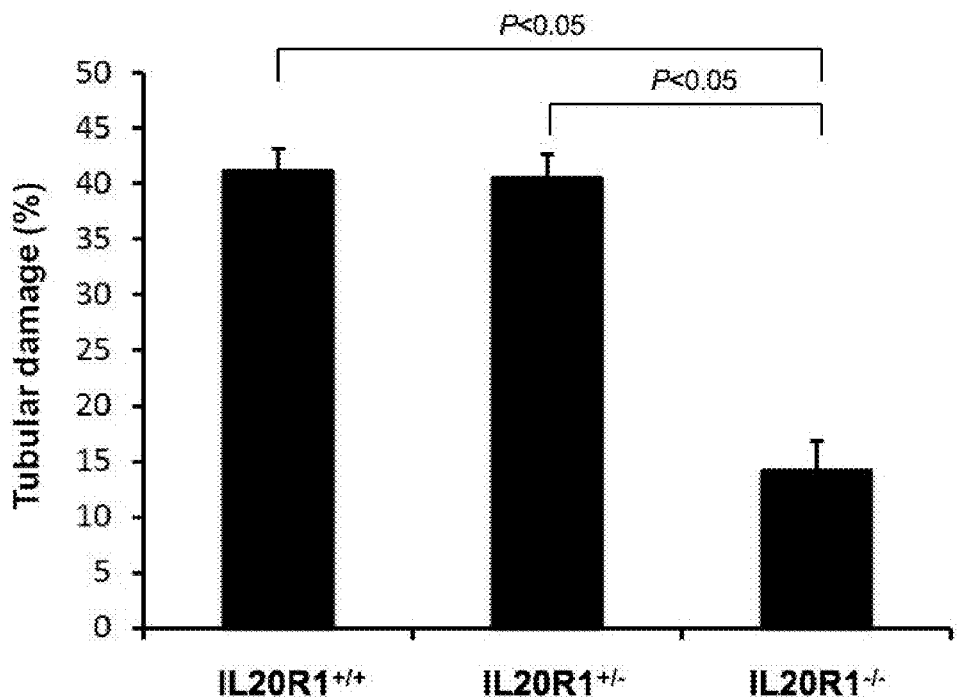

Typically, HgCl$_2$-treated mice exhibited increased BUN levels and renal tubular damage, both being indicators of renal dysfunction. In this study, an increased BUN level was observed in the IL-20R1$^{+/+}$ mice treated with HgCl$_2$. Differently, the BUN level in the HgCl$_2$-treated IL-20R1$^{-/-}$ mice was much lower than that in the IL-20R1$^{+/+}$ mice. See FIG. 3, panel A (P<0.05). The level of tubular damage was also much lower in the HgCl$_2$-treated IL-20R1$^{-/-}$ mice as compared to the IL-20R1$^{+/+}$ mice. See FIG. 3, panel B. These results clearly indicate that the severity of HgCl$_2$-induced renal failure is much lower in IL-20R1 knockout mice than in normal mice. Accordingly, suppression the IL-20 receptor activity would be effective in treating acute renal failure.

EXAMPLE 3

Reduced Severity of STZ-Induced Diabetic Nephropathy in IL-20R1 Knockout Mice

Figure 4:
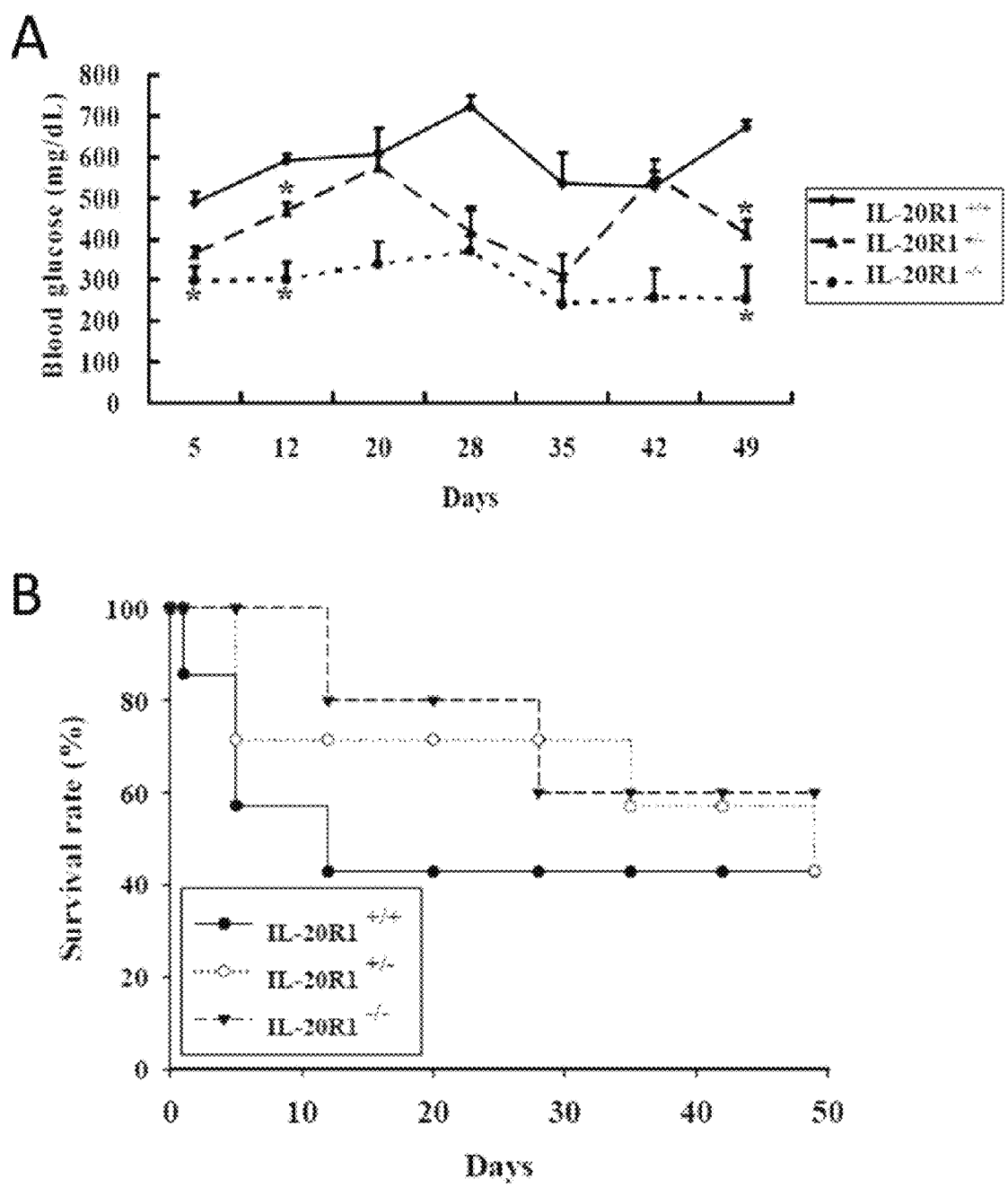
FIG. 4 is a diagram showing severity of STZ-induced diabetic nephropathy in IL-20R1$^{+/+}$, IL-20R1$^{+/-}$, and IL-20R1$^{-/-}$ mice. Panel A: Blood glucose levels. Panel B.
Figure 4:
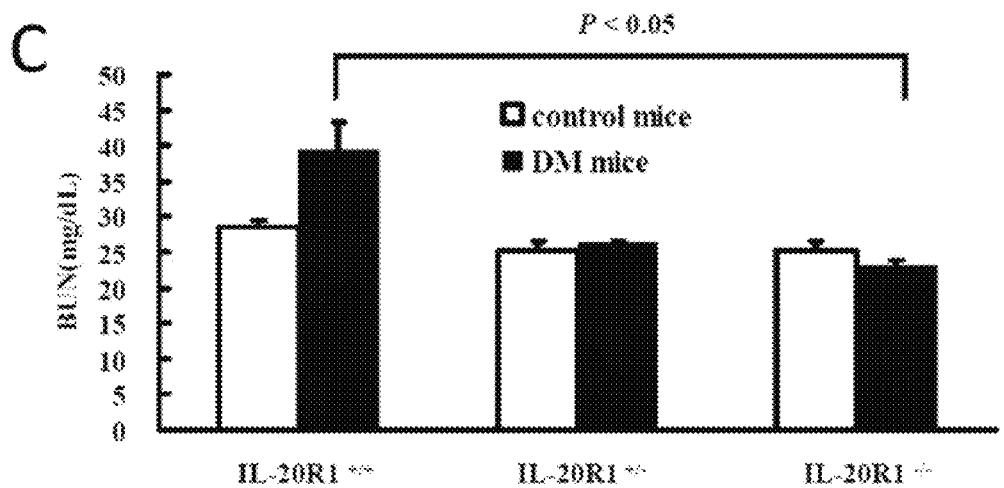
Figure 4:
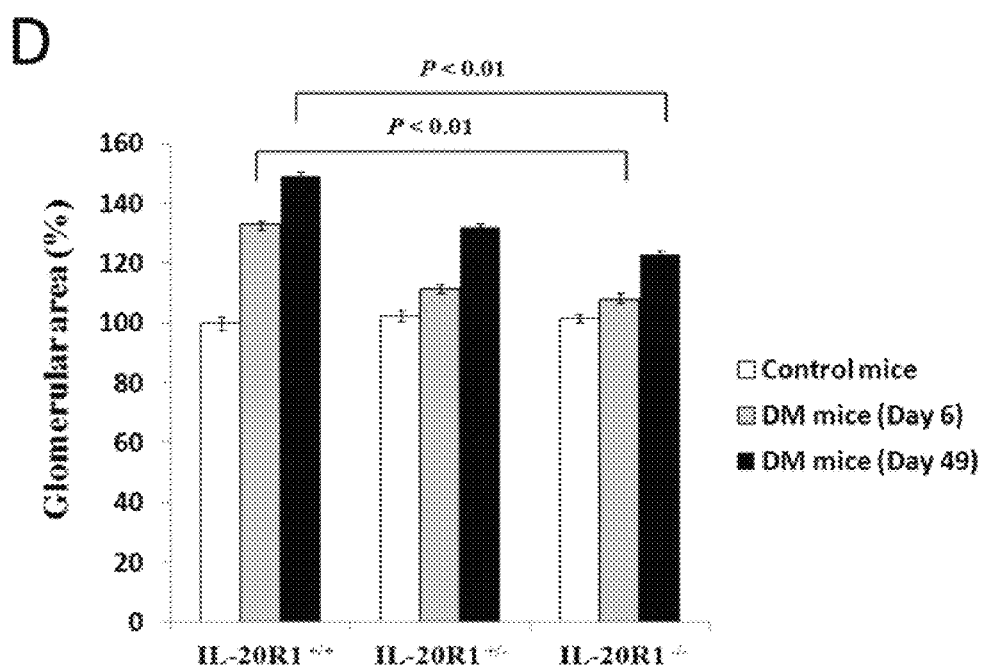

Diabetes was induced in the IL-20R1$^{+/+}$, IL-20R1$^{+/-}$, and IL-20R1$^{-/-}$ mice mentioned in Example 1 above by streptozotocin (STZ), following the method described in Rossini A A, et al., *Proc Natl Acad Sci USA* 74:2485-2489, 1977. Typically, STZ-treated mice display increased glucose levels, serum BUN levels, and enlarged glomeruli. Here, the STZ-treated IL-20R1$^{-/-}$ mice showed much lower blood glucose levels as compared to the STZ-treated IL-20R1$^{+/+}$ mice. See FIG. 4, panel A (P<0.05). The survival rate of the IL-20R1$^{-/-}$ mice was significantly higher than that of the IL-20R1$^{+/+}$ mice at day 27 post STZ treatment. See FIG. 4, panel B. The serum BUN levels in the STZ-treated IL-20R1$^{-/-}$ mice were lower than those in the STZ-treated IL-20R1$^{+/+}$ mice, indicating an improved renal function. See FIG. 4, panel C.

Glomerular enlargement during diabetes is an indication of renal damage. Here, the average glomerular area was lower in the STZ-treated IL-20R1$^{-/-}$ mice as compared to wild type IL-20R1$^{+/+}$ mice treated with STZ on day 6 and day 49. See FIG. 4, panel D.

In sum, the results obtained from this study indicate that knocking out IL-20R1, thereby eliminating the activity of IL-20 receptor, unexpectedly reduced blood glucose levels and severity of diabetic nephropathy. Thus, suppression of IL-20 receptor activity would be effective in improving diabetic nephropathy.

EXAMPLE 4 mAb7GW and mAb51D Inhibited Osteoclast Differentiation

Bone marrow cells (BMCs) from the tibias of mice were incubated for 12 h (37° C./5% CO$_2$). Non-adherent cells were collected and seeded in 24-well plates (2×10$^6$ cells per well) and cultured in the same medium supplemented with 30 ng/ml of recombinant murine macrophage colony-stimulating factor (M-CSF) (PeproTech). After 48 h, M-CSF-derived osteoclast precursor cells were cultured with murine M-CSF (40 ng/ml) and sRANKL (100 ng/ml) (PeproTech) until the end of the experiment. To analyze the effect of IL-20 R1 monoclonal antibody in osteoclast differentiation, M-CSF-derived osteoclast precursor cells were treated with mAb7GW (1 or 2 ug/ml) or 51D (1 or 2 ug/ml) or mIgG (2 ug/ml) as a negative control in α-MEM with M-CSF and sRANKL for 8 days. The culture medium was changed every 2 days in all differentiation experiments. To calculate the number of osteoclasts, the cells were fixed in acetone and stained for TRAP using an acid phosphatase kit (Sigma-Aldrich). TRAP-positive multinucleated cells containing three or more nuclei were considered to be osteoclasts.

As shown in FIG. 5, both mAb7GW and mAb51D successfully inhibited osteoclast differentiation, indicating that these two monoclonal antibodies can be used for treating osteoporosis, as well as other metabolic bone diseases involving bone resorption or cancer-induced osteolysis.

EXAMPLE 5 mAb7GW and mAb51D Inhibited IL-19 induced CE81T Cell Proliferation

Human esophagus cancer cell line CE81T ($3 \times 10^4$ cells) were seeded in the DMEM medium with high glucose and 10% fetal calf serum (FBS) for 12 hours followed by starvation for 8 hours without FBS. Cells were then treated with human IL-19 (400 ng/ml) together with the anti IL-20 R1 monoclonal antibody mAb7GW (4 ug/ml) or mAb51D (4 ug/ml) and then incubated for 48 hrs. Positive control group was treated with 5% FBS alone. Cell proliferation was analyzed by adding MTT (0.35 mg/ml) for 3 hours followed by DMSO. Absorbency at 550 nm was measured and compared with the control.

As shown in FIG. 6, both mAb7GW and mAb51D inhibited IL-19-induced CE81T cell proliferation. This indicates that both monoclonal antibodies can block the signaling pathway triggered by IL-19 by binding to IL-20R1.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

What is claimed is:

1. A method for treating osteoporosis, comprising administering to a subject in need thereof an effective amount of an anti-IL-20 receptor antibody.

2. The method of claim 1, wherein the antibody binds to IL-20R1.

3. The method of claim 2, wherein the antibody is a whole immunoglobulin molecule, an antigen-binding fragment thereof, a humanized antibody, a chimeric antibody, or an scFv.

4. The method of claim 2, wherein the antibody is a bi-specific antibody that binds to both IL-20R1 and IL-19, IL-20, or IL-20R2.

5. The method of claim 2, wherein the antibody comprises (i) a heavy chain variable region containing the same complementarity determining regions (CDRs) as those in the heavy chain variable region of monoclonal antibody mAb7GW and a light chain variable region containing the same CDRs as those in the light chain variable region of mAb7GW; or (ii) a heavy chain variable region containing the same CDRs as those in the heavy chain variable region of monoclonal antibody mAb51D and a light chain variable region containing the same CDRs as those in the light chain variable region of mAb51D.

6. The method of claim 2, wherein the antibody comprises (i) the heavy chain variable region and the light chain variable region of mAb7GW; or (ii) the heavy chain variable region and the light chain variable region of mAb51D.

7. The method of claim 2, wherein the antibody is a humanized antibody of mAb7GW or mAb51D.

* * * * *

SEQUENCE LISTING

```
<160> NUMBER OF SEQ ID NOS: 8

<210> SEQ ID NO 1
<211> LENGTH: 457
<212> TYPE: PRT
<213> ORGANISM: Mouse

<400> SEQUENCE: 1

Met Arg Val Leu Ile Leu Leu Trp Leu Phe Thr Ala Phe Pro Gly Ile
1               5                   10                  15

Leu Ser Val Val Gln Leu Gln Glu Ser Gly Pro Gly Leu Val Lys Pro
            20                  25                  30

Ser Gln Ser Leu Ser Leu Thr Cys Thr Val Thr Gly Tyr Ser Ile Thr
        35                  40                  45

Ser Asp Tyr Ala Trp Asn Trp Ile Arg Gln Phe Pro Gly Asn Arg Leu
    50                  55                  60

Glu Trp Met Gly Tyr Ile Asp Tyr Ser Gly Ser Thr Lys Tyr Asn Pro
65                  70                  75                  80

Ser Leu Lys Ser Arg Ile Ser Val Thr Arg Asp Thr Ser Lys Asn Gln
                85                  90                  95

Phe Phe Leu Gln Leu Asn Ser Val Thr Thr Glu Asp Thr Ala Thr Tyr
            100                 105                 110

Tyr Cys Ala Arg Asp Phe Gly Asp Ala Tyr Trp Gly Gln Gly Thr Leu
        115                 120                 125

Val Thr Val Ser Ala Ala Lys Thr Thr Pro Pro Ser Val Tyr Pro Leu
    130                 135                 140

Ala Pro Gly Ser Ala Ala Gln Thr Asn Ser Met Val Thr Leu Gly Cys
145                 150                 155                 160

Leu Val Lys Gly Tyr Phe Pro Glu Pro Val Thr Val Thr Trp Asn Ser
                165                 170                 175

Gly Ser Leu Ser Ser Gly Val His Thr Phe Pro Ala Val Leu Gln Ser
            180                 185                 190

Asp Leu Tyr Thr Leu Ser Ser Val Thr Val Pro Ser Ser Thr Trp
        195                 200                 205

Pro Ser Glu Thr Val Thr Cys Asn Val Ala His Pro Ala Ser Ser Thr
    210                 215                 220

Lys Val Asp Lys Lys Ile Val Pro Arg Asp Cys Gly Cys Lys Pro Cys
225                 230                 235                 240
```

Ile Cys Thr Val Pro Glu Val Ser Ser Val Phe Ile Phe Pro Pro Lys
            245                 250                 255

Pro Lys Asp Val Leu Thr Ile Thr Leu Thr Pro Lys Val Thr Cys Val
        260                 265                 270

Val Val Asp Ile Ser Lys Asp Asp Pro Glu Val Gln Phe Ser Trp Phe
    275                 280                 285

Val Asp Asp Val Glu Val His Thr Ala Gln Thr Gln Pro Arg Glu Glu
290                 295                 300

Gln Phe Asn Ser Thr Phe Arg Ser Val Ser Glu Leu Pro Ile Met His
305                 310                 315                 320

Gln Asp Trp Leu Asn Gly Lys Glu Phe Lys Cys Arg Val Asn Ser Ala
                325                 330                 335

Ala Phe Pro Ala Pro Ile Glu Lys Thr Ile Ser Lys Thr Lys Gly Arg
            340                 345                 350

Pro Lys Ala Pro Gln Val Tyr Thr Ile Pro Pro Pro Lys Glu Gln Met
        355                 360                 365

Ala Lys Asp Lys Val Ser Leu Thr Cys Met Ile Thr Asp Phe Phe Pro
370                 375                 380

Glu Asp Ile Thr Val Glu Trp Gln Trp Asn Gly Gln Pro Ala Glu Asn
385                 390                 395                 400

Tyr Lys Asn Thr Gln Pro Ile Met Asp Thr Asp Gly Ser Tyr Phe Val
                405                 410                 415

Tyr Ser Lys Leu Asn Val Gln Lys Ser Asn Trp Glu Ala Gly Asn Thr
            420                 425                 430

Phe Thr Cys Ser Val Leu His Glu Gly Leu His Asn His His Thr Glu
        435                 440                 445

Lys Ser Leu Ser His Ser Pro Gly Lys
    450                 455

<210> SEQ ID NO 2
<211> LENGTH: 1374
<212> TYPE: DNA
<213> ORGANISM: mouse

<400> SEQUENCE: 2
atgagagtgc tgattctttt gtggctgttc acagcctttc ctggtatcct gtctgttgtg      60
cagcttcagg agtcgggacc tggcctggtg aaaccttctc agtctctgtc cctcacctgc     120
actgtcactg gctactcaat caccagtgat tatgcctgga actggatccg gcagttccca     180
ggaaacagac tggagtggat gggctacata gactacagtg gtagcactaa atacaacccc     240
tctctcaaaa gtcgaatctc tgtcactcga gacacatcca agaaccagtt cttcctgcag     300
ttgaattctg tgactactga ggacacagcc acatattact gtgcaagaga ctttggtgat     360
gcttactggg gccaggggac tctggtcact gtctctgcag ccaaaacgac cccccatct     420 gtctatccac tggcccctgg atctgctgcc caaactaact ccatggtgac cctgggatgc     480
ctggtcaagg gctatttccc tgagccagtg acagtgacct ggaactctgg atccctgtcc     540
agcggtgtgc acaccttccc agctgtcctg cagtctgacc tctacactct gagcagctca     600
gtgactgtcc cctccagcac ctggcccagc gagaccgtca cctgcaacgt tgcccacccg     660
gccagcagca ccaaggtgga caagaaaatt gtgcccaggg attgtggttg taagccttgc     720
atatgtacag tcccagaagt atcatctgtc ttcatcttcc ccccaaagcc caaggatgtg     780
ctcaccatta ctctgactcc taaggtcacg tgtgttgtgg tagacatcag caaggatgat     840

| | | |
|---|---|---|
| cccgaggtcc agttcagctg gtttgtagat gatgtggagg tgcacacagc tcaaacgcaa | 900 | |
| ccccgggagg agcagttcaa cagcactttc cgctcagtca gtgaacttcc catcatgcac | 960 | |
| caggactggc tcaatggcaa ggagttcaaa tgcagggtca acagtgcagc tttccctgcc | 1020 | |
| cccatcgaga aaaccatctc caaaaccaaa ggcagaccga aggctccaca ggtgtacacc | 1080 | |
| attccacctc ccaaggagca aatggccaag gataaagtca gtctgacctg catgataaca | 1140 | |
| gacttcttcc ctgaagacat tactgtggag tggcagtgga atgggcagcc agcggagaac | 1200 | |
| tacaagaaca ctcagcccat catggacaca gatggctctt acttcgtcta cagcaagctc | 1260 | |
| aatgtgcaga gagcaactg ggaggcagga aatactttca cctgctctgt gttacatgag | 1320 | |
| ggcctgcaca accaccatac tgagaagagc ctctcccact ctcctggtaa atga | 1374 | |

<210> SEQ ID NO 3
<211> LENGTH: 240
<212> TYPE: PRT
<213> ORGANISM: mouse

<400> SEQUENCE: 3

Met Asp Ser Gln Ala Gln Val Leu Met Leu Leu Leu Trp Val Ser
1               5                   10                  15

Gly Ser Cys Gly Asp Ile Val Met Ser Gln Ser Pro Ser Ser Leu Ala
                20                  25                  30

Val Ser Val Gly Glu Lys Val Thr Met Ser Cys Lys Ser Ser Gln Ser
            35                  40                  45

Leu Leu Tyr Ser Arg Asn Gln Lys Asn Tyr Leu Ala Trp Tyr Gln Leu
        50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Ala Glu Asp Leu Ala Val Tyr
            100                 105                 110

Tyr Cys Gln Gln Tyr Tyr Ser Tyr Pro Leu Thr Phe Gly Ala Gly Thr
        115                 120                 125

Lys Leu Glu Leu Lys Arg Ala Asp Ala Ala Pro Thr Val Ser Ile Phe
130                 135                 140

Pro Pro Ser Ser Glu Gln Leu Thr Ser Gly Gly Ala Ser Val Val Cys
145                 150                 155                 160

Phe Leu Asn Asn Phe Tyr Pro Lys Asp Ile Asn Val Lys Trp Lys Ile
                165                 170                 175

Asp Gly Ser Glu Arg Gln Asn Gly Val Leu Asn Ser Trp Thr Asp Gln
            180                 185                 190

Asp Ser Lys Asp Ser Thr Tyr Ser Met Ser Ser Thr Leu Thr Leu Thr
        195                 200                 205

Lys Asp Glu Tyr Glu Arg His Asn Ser Tyr Thr Cys Glu Ala Thr His
210                 215                 220

Lys Thr Ser Thr Ser Pro Ile Val Lys Ser Phe Asn Arg Asn Glu Cys
225                 230                 235                 240

<210> SEQ ID NO 4
<211> LENGTH: 723
<212> TYPE: DNA
<213> ORGANISM: mouse

<400> SEQUENCE: 4

```
atggattcac aggcccaggt tcttatgtta ctgctgctat gggtatctgg ttcctgtggg      60
gacattgtga tgtcacagtc tccatcctcc ctagctgtgt cagttggaga gaaggttact     120
atgagctgca agtccagtca gagccttttta tatagtagga atcaaaagaa ctacttggcc    180
tggtaccagc tgaagccagg gcagtctcct aaactgctga tttactgggc atccactagg    240
gaatctgggg tccctgatcg cttcacaggc agtggatctg ggacagattt cactctcacc    300
atcagcagtg tgaaggctga agacctggca gtttattact gtcagcaata ttatagctat    360
ccgctcacgt tcggtgctgg gaccaagctg gagctgaaac gggctgatgc tgcaccaact    420
gtatccatct tcccaccatc cagtgagcag ttaacatctg gaggtgcctc agtcgtgtgc    480
ttcttgaaca acttctaccc caaagacatc aatgtcaagt ggaagattga tggcagtgaa    540
cgacaaaatg gcgtcctgaa cagttggact gatcaggaca gcaaagacag cacctacagc    600
atgagcagca ccctcacgtt gaccaaggac gagtatgaac gacataacag ctatacctgt    660
gaggccactc acaagacatc aacttcaccc attgtcaaga gcttcaacag gaatgagtgt    720
tag                                                                   723
```

<210> SEQ ID NO 5
<211> LENGTH: 460
<212> TYPE: PRT
<213> ORGANISM: mouse

<400> SEQUENCE: 5

```
Met Asn Phe Gly Leu Ser Leu Ile Phe Leu Ala Leu Ile Leu Lys Gly
1               5                   10                  15

Val Gln Cys Glu Val Gln Leu Val Glu Ala Gly Gly Asp Leu Val Lys
            20                  25                  30

Pro Gly Gly Ser Leu Lys Leu Ser Cys Ala Ala Ser Gly Phe Ser Leu
        35                  40                  45

Ser Asn Tyr Gly Met Ser Trp Val Arg Gln Thr Pro Asp Lys Arg Leu
    50                  55                  60

Glu Trp Val Ala Ser Ile Ser Ser Gly Gly Arg Phe Thr Ser Tyr Pro
65                  70                  75                  80

Asp Ser Val Arg Gly Arg Phe Thr Ile Ser Arg Asp Asn Ala Lys Asn
                85                  90                  95

Thr Leu Tyr Leu Gln Met Ser Gly Leu Lys Ser Glu Asp Thr Ala Met
            100                 105                 110

Tyr Tyr Cys Ala Arg His Asp Gly Asn Gly Gly Asp Tyr Trp Gly Gln
        115                 120                 125

Gly Thr Ser Val Thr Val Ser Ser Ala Lys Thr Thr Pro Pro Ser Val
    130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Pro Ser
        195                 200                 205

Ser Thr Trp Pro Ser Glu Thr Val Thr Cys Asn Val Ala His Pro Ala
    210                 215                 220

Ser Ser Thr Lys Val Asp Lys Lys Ile Val Pro Arg Asp Cys Gly Cys
225                 230                 235                 240
```

```
Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
            260                 265                 270

Thr Cys Val Val Val Asp Ile Ser Lys Asp Asp Pro Glu Val Gln Phe
        275                 280                 285

Ser Trp Phe Val Asp Asp Val Glu Val His Thr Ala Gln Thr Gln Pro
    290                 295                 300

Arg Glu Glu Gln Phe Asn Ser Thr Phe Arg Ser Val Ser Glu Leu Pro
305                 310                 315                 320

Ile Met His Gln Asp Trp Leu Asn Gly Lys Glu Phe Lys Cys Arg Val
                325                 330                 335

Asn Ser Ala Ala Phe Pro Ala Pro Ile Glu Lys Thr Ile Ser Lys Thr
            340                 345                 350

Lys Gly Arg Pro Lys Ala Pro Gln Val Tyr Thr Ile Pro Pro Pro Lys
        355                 360                 365

Glu Gln Met Ala Lys Asp Lys Val Ser Leu Thr Cys Met Ile Thr Asp
    370                 375                 380

Phe Phe Pro Glu Asp Ile Thr Val Glu Trp Gln Trp Asn Gly Gln Pro
385                 390                 395                 400

Ala Glu Asn Tyr Lys Asn Thr Gln Pro Ile Met Asp Thr Asp Gly Ser
                405                 410                 415

Tyr Phe Val Tyr Ser Lys Leu Asn Val Gln Lys Ser Asn Trp Glu Ala
            420                 425                 430

Gly Asn Thr Phe Thr Cys Ser Val Leu His Glu Gly Leu His Asn His
        435                 440                 445

His Thr Glu Lys Ser Leu Ser His Ser Pro Gly Lys
    450                 455                 460

<210> SEQ ID NO 6
<211> LENGTH: 1383
<212> TYPE: DNA
<213> ORGANISM: mouse

<400> SEQUENCE: 6
atgaacttcg ggctcagcct gattttcctt gccctcattt taaaggtgt ccagtgtgag    60 gtgcagctgg tggaggctgg gggagactta gtgaagcctg agggtccct gaaactctcc   120 tgtgcggcct ctggattcag tttgagtaac tatggcatgt cctgggttcg ccagactcca   180
gacaagaggc tggagtgggt cgcaagcatt agtagtggtg gtcgtttcac ctcctatcca   240
gacagtgtga gggggcgatt caccatctcc agagacaatg ccaagaacac cctgtacctg   300
caaatgagcg tctgaagtc tgaggacaca gccatgtatt actgtgcaag acacgacggc   360
aacggtgggg actactgggg tcaaggaacc tcagtcaccg tctcctcagc caaaacgaca   420
cccccatctg tctatccact ggcccctgga tctgctgccc aaactaactc catggtgacc   480
ctgggatgcc tggtcaaggg ctatttccct gagccagtga cagtgacctg aactctgga   540 tccctgtcca gcggtgtgca ccttcccca gctgtcctgc agtctgacct ctacactctg   600
agcagctcag tgactgtccc ctccagcacc tggcccagcg agaccgtcac ctgcaacgtt   660
gcccacccgg ccagcagcac caaggtggac aagaaaattg tgcccaggga ttgtggttgt   720
aagccttgca tatgtacagt cccagaagta tcatctgtct tcatcttccc cccaaagccc   780
aaggatgtgc tcaccattac tctgactcct aaggtcacgt gtgttgtggt agacatcagc   840
aaggatgatc ccgaggtcca gttcagctgg tttgtagatg atgtggaggt gcacacagct   900
```

```
cagacgcaac cccgggagga gcagttcaac agcactttcc gctcagtcag tgaacttccc    960
atcatgcacc aggactggct caatggcaag gagttcaaat gcagggtcaa cagtgcagct   1020
ttccctgccc ccatcgagaa aaccatctcc aaaaccaaag gcagaccgaa ggctccacag   1080
gtgtacacca ttccacctcc caaggagcag atggccaagg ataaagtcag tctgacctgc   1140
atgataacag acttcttccc tgaagacatt actgtggagt ggcagtggaa tgggcagcca   1200
gcggagaact acaagaacac tcagcccatc atggacacag atggctctta cttcgtctac   1260
agcaagctca atgtgcagaa gagcaactgg gaggcaggaa atactttcac ctgctctgtg   1320
ttacatgagg gcctgcacaa ccaccatact gagaagagcc tctcccactc tcctggtaaa   1380
tga                                                                 1383
```

<210> SEQ ID NO 7
<211> LENGTH: 235
<212> TYPE: PRT
<213> ORGANISM: mouse

<400> SEQUENCE: 7

Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Phe Pro Ala Ile
            20                  25                  30

Leu Ser Ala Ser Pro Gly Glu Lys Val Thr Met Thr Cys Arg Ala Arg
        35                  40                  45

Ser Ser Val Ser Phe Met His Trp Tyr Gln Lys Pro Gly Ser Ser
    50                  55                  60

Pro Lys Pro Trp Ile Tyr Ala Thr Ser Asn Leu Ala Ser Gly Val Pro
65                  70                  75                  80

Pro Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Ser Asn Pro Tyr Thr Phe Gly Gly Gly Thr Lys Leu Glu Ile Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Cys
225                 230                 235

<210> SEQ ID NO 8
<211> LENGTH: 708
<212> TYPE: DNA
<213> ORGANISM: mouse

<400> SEQUENCE: 8

```
atggattttc aagtgcagat tttcagcttc ctgctaatca gtgcttcagt cataatgtcc      60
agaggacaaa ttgttctctc ccagtttcca gcaatcctgt ctgcatctcc aggggagaag     120
gtcacaatga cttgcagggc caggtcaagt gtaagtttca tgcactggta ccagcagaag     180
ccaggatcct cccccaaacc ctggatttat gccacatcca acctggcttc tggagtccct     240
cctcgcttca gtggcagtgg gtctgggacc tcttactctc tcacaatcag cagagtggag     300
gctgaagatg ctgccactta ttactgccag cagtggagta gtaacccata cacgttcgga     360 gggggggacta agctggaaat aaaacgggct gatgctgcac caactgtatc catcttccca     420
ccatccagtg agcagttaac atctggaggt gcctcagtcg tgtgcttctt gaacaacttc     480 tacccccaaag acatcaatgt caagtggaag attgatggca gtgaacgaca aaatggcgtc     540
ctgaacagtt ggactgatca ggacagcaaa gacagcacct acagcatgag cagcaccctc     600
acgttgacca aggacgagta tgaacgacat aacagctata cctgtgaggc cactcacaag     660
acatcaactt cacccattgt caagagcttc aacaggaatg agtgttag              708
```